United States Patent
Kerem et al.

(10) Patent No.: US 10,731,156 B2
(45) Date of Patent: *Aug. 4, 2020

(54) RESTORATION OF THE CFTR FUNCTION BY SPLICING MODULATION

(71) Applicant: Yissum Research Development Company of the Hebrew University of Jerusalem Ltd., Jerusalem (IL)

(72) Inventors: Batsheva Kerem, Mevaseret Zion (IL); Michal Tur Sinai, Mevaseret Zion (IL); Loren Price, Wembley (AU); Stephen Donald Wilton, Applecross (AU); Sue Fletcher, Bayswater (AU)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/869,664

(22) Filed: Jan. 12, 2018

(65) Prior Publication Data
US 2018/0155723 A1    Jun. 7, 2018

Related U.S. Application Data

(63) Continuation of application No. 14/667,285, filed on Mar. 24, 2015, now Pat. No. 10,428,328, which is a
(Continued)

(51) Int. Cl.
*A61K 48/00* (2006.01)
*C07H 21/02* (2006.01)
(Continued)

(52) U.S. Cl.
CPC ........ *C12N 15/113* (2013.01); *A61K 31/7105* (2013.01); *A61K 45/06* (2013.01);
(Continued)

(58) Field of Classification Search
CPC .............. C12N 15/113; C12N 15/1137; C12N 2310/11; C12N 2320/33; C12N 2320/21; A61K 31/7105
See application file for complete search history.

(56) References Cited

U.S. PATENT DOCUMENTS 5,580,969 A    12/1996  Hoke et al.
7,176,303 B2 *  2/2007  Freier ................... C07H 21/02
                                                              435/5
(Continued)

FOREIGN PATENT DOCUMENTS

EP    0 636 137 B1    3/1997
WO    00/09734 A2    2/2000
(Continued)

OTHER PUBLICATIONS

Mansfield et al., (2000) Repair of CFTR mRNA by spliceosome-mediated RNA trans-splicing. Gene Ther 7(22): 1885-1895.
(Continued)

*Primary Examiner* — Terra C Gibbs
(74) *Attorney, Agent, or Firm* — The Roy Gross Law Firm, LLC; Roy Gross

(57) ABSTRACT

Provided are oligonucleotides capable of binding to and modulating the splicing of the pre-mRNA of the CFTR gene, compositions including said oligonucleotides, kits including the compositions, and uses thereof. In particular, the subject matter provides compositions of oligonucleotides useful in methods for suppressing exon skipping optionally in combination with additional CFTR therapeutics.

20 Claims, 9 Drawing Sheets

Specification includes a Sequence Listing.

Related U.S. Application Data continuation of application No. PCT/IL2013/050789, filed on Sep. 17, 2013.

(60) Provisional application No. 61/704,859, filed on Sep. 24, 2012.

(51) Int. Cl.
*C07H 21/04* (2006.01)
*A61K 31/7105* (2006.01)
*A61K 45/06* (2006.01)
*C12N 15/11* (2006.01)
*C12N 15/113* (2010.01)

(52) U.S. Cl.
CPC ...... *C12N 15/1138* (2013.01); *C12N 2310/11* (2013.01); *C12N 2310/315* (2013.01); *C12N 2310/321* (2013.01); *C12N 2320/31* (2013.01); *C12N 2320/33* (2013.01)

(56) References Cited

U.S. PATENT DOCUMENTS

| | | | | |
|---|---|---|---|---|
| 8,501,703 | B2 * | 8/2013 | Bennett | C12N 15/111 514/44 A |
| 9,157,081 | B2 | 10/2015 | Bennett et al. | |
| 10,428,328 | B2 * | 10/2019 | Kerem | A61K 31/7105 |

FOREIGN PATENT DOCUMENTS

| | | | |
|---|---|---|---|
| WO | 03/074737 A1 | 9/2003 | |
| WO | 2008074023 | 6/2008 | |
| WO | WO-2008074023 A2 * | 6/2008 | ........... C12Q 1/6818 |

OTHER PUBLICATIONS

Mendell et al., (2013) Eteplirsen for the treatment of Duchenne muscular dystrophy. Ann Neurol 74(5): 637-647.
Mitrpant et al., (2009) Rational design of antisense oligomers to induce dystrophin exon skipping. Mol Ther 17(8): 1418-1426.
Porensky et al., (2012) A single administration of morpholino antisense oligomer rescues spinal muscular atrophy in mouse. Hum Mol Genet 21(7): 1625-1638.
Price et al., (2013) "Silencing a disease modifying mutation for cystic fibrosis using antisense oligonucleotides". The Journal of Gene Medicine 15: 311-340. 8th Australian Gene Therapy Society Meeting, May 8-May 10, 2013. p. 338.
Rogan et al., (2011) Cystic fibrosis transmembrane conductance regulator intracellular processing, trafficking, and opportunities for mutation-specific treatment. Chest 139(6): 1480-1490.
Sazani et al., (2003) Therapeutic potential of antisense oligonucleotides as modulators of alternative splicing. J Clin Invest 112(4): 481-486.
Singh et al., (2009) A short antisense oligonucleotide masking a unique intronic motif prevents skipping of a critical exon in spinal muscular atrophy. RNA Biol 6(3): 341-350.
Tsui, (1992) The spectrum of cystic fibrosis mutations. Trends Genet 8(11): 392-398.
Tsui et al., (2013) The cystic fibrosis gene: a molecular genetic perspective. Cold Spring Harb Perspect Med 3(2): a009472; 16 pages.
Van Deutekom et al., (2007) Local dystrophin restoration with antisense oligonucleotide PRO051. N Engl J Med 357 (26): 2677-2686.
Williams et al., (2009) Oligonucleotide-mediated survival of motor neuron protein expression in CNS improves phenotype in a mouse model of spinal muscular atrophy. J Neurosci 29(24): 7633-7638.
Flume et al., (2012) Ivacaftor in subjects with cystic fibrosis who are homozygous for the F508del-CFTR mutation. Chest 142(3):718-724.

GeneBank Accession No. NG_016465.4, downloaded from https://www.ncbi.nlm.nih.gov/nuccore/NG_016465.4 on Apr. 15, 2018; 61 pages.
Augarten et al., (1993) Mild cystic fibrosis and normal or borderline sweat test in patients with the 3849 + 10 kb C—>T mutation. Lancet 342(8862): 25-26.
Braasch et al., (2002) Antisense inhibition of gene expression in cells by oligonucleotides incorporating locked nucleic acids: effect of mRNA target sequence and chimera design. Nucleic Acids Res 30(23): 5160-5167.
Chiba-Falek et al., (1998) The molecular basis of disease variability among cystic fibrosis patients carrying the 3849 + 10 kb C—>T mutation. Genomics 53(3): 276-283.
Chu et al., (1993) Genetic basis of variable exon 9 skipping in cystic fibrosis transmembrane conductance regulator mRNA. Nat Genet 3(2): 151-156.
Cutrona et al., (2000) Effects in live cells of a c-myc anti-gene PNA linked to a nuclear localization signal. Nat Biotechnol 18(3): 300-303 abstract.
Debotton et al., (2008) Overcoming the formulation obstacles towards targeted chemotherapy: in vitro and in vivo evaluation of cytotoxic drug loaded immunonanoparticles. J Control Release 127(3): 219-230.
Hagigit et al., (2010) Topical and intravitreous administration of cationic nanoemulsions to deliver antisense oligonucleotides directed towards VEGF KDR receptors to the eye. J Control Release 145(3): 297-305.
Heemskerk et al., (2010) Preclinical PK and PD studies on 2'-O-methyl-phosphorothioate RNA antisense oligonucleotides in the mdx mouse model. Mol Ther 18(6): 1210-1217.
Highsmith et al., (1994) A novel mutation in the cystic fibrosis gene in patients with pulmonary disease but normal sweat chloride concentrations. N Engl J Med 331(15): 974-980.
Kerem et al., (1997) A cystic fibrosis transmembrane conductance regulator splice variant with partial penetrance associated with variable cystic fibrosis presentations. Am J Respir Crit Care Med 155(6): 1914-1920.
Kole et al., (2012) RNA therapeutics: beyond RNA interference and antisense oligonucleotides. Nat Rev Drug Discov 11(2): 125-140.
Larsen et al., (1999) Antisense properties of peptide nucleic acid. Biochim Biophys Acta 1489(1): 159-166.
Linde et al., (2007) Nonsense-mediated mRNA decay affects nonsense transcript levels and governs response of cystic fibrosis patients to gentamicin. J Clin Invest 117(3): 683-692.
Mann et al., (2002) Improved antisense oligonucleotide induced exon skipping in the mdx mouse model of muscular dystrophy. J Gene Med 4(6): 644-654.
Nissim-Rafinia et al., (2002) Splicing regulation as a potential genetic modifier. Trends Genet 18(3): 123-127.
Nissim-Rafinia et al., (2005) The splicing machinery is a genetic modifier of disease severity. Trends Genet 21(9): 480-483.
Nissim-Rafinia et al., (2000) Cellular and viral splicing factors can modify the splicing pattern of CFTR transcripts carrying splicing mutations. Hum Mol Genet 9(12): 1771-1778.
Nissim-Rafinia et al., (2004) Restoration of the cystic fibrosis transmembrane conductance regulator function by splicing modulation. EMBO Rep 5(11): 1071-1077.
Rave-Harel et al., (1997) The molecular basis of partial penetrance of splicing mutations in cystic fibrosis. Am J Hum Genet 60(1): 87-94.
Rowe et al., (2007) Restoration of W1282X CFTR activity by enhanced expression. Am J Respir Cell Mol Biol 37(3): 347-356.
Rowe et al., (2010) DeltaF508 CFTR processing correction and activity in polarized airway and non-airway cell monolayers. Pulm Pharmacol Ther 23(4): 268-278.
Sloane et al., (2012) A pharmacologic approach to acquired cystic fibrosis transmembrane conductance regulator dysfunction in smoking related lung disease. PLoS One 7(6): e39809; 19 pages.
Teixeira et al., (1999) Submicron cationic emulsions as a new delivery system for oligonucleotides. Pharm Res 16 (1): 30-36.
Yin et al., (2008) Effective exon skipping and restoration of dystrophin expression by peptide nucleic acid antisense oligonucleotides in mdx mice. Mol Ther 16(1): 38-45.

(56) References Cited

OTHER PUBLICATIONS

Yin et al., (2010) Optimization of peptide nucleic acid antisense oligonucleotides for local and systemic dystrophin splice correction in the mdx mouse. Mol Ther 18(4): 819-827.
BECQ (2010) Cystic fibrosis transmembrane conductance regulator modulators for personalized drug treatment of cystic fibrosis. Drugs 70(3): 241-259.
Buratti et al., (2007) SR protein-mediated inhibition of CFTR exon 9 inclusion: molecular characterization of the intronic splicing silencer. Nucleic acids research 35(13): 4359-4368.
Cirak et al., (2011) Exon skipping and dystrophin restoration in patients with Duchenne muscular dystrophy after systemic phosphorodiamidate morpholino oligomer treatment: an open-label, phase 2, dose-escalation study. Lancet 378(9791): 595-605.
Cutting et al., (1990) A cluster of cystic fibrosis mutations in the first nucleotide-binding fold of the cystic fibrosis conductance regulator protein. Nature 346(6282): 366-369.
Dhir et al. (2010) Alternative splicing: role of pseudoexons in human disease and potential therapeutic strategies. FEBS J 277(4): 841-855.
El-Seedy et al., (2009) Influence of the duplication of CFTR exon 9 and its flanking sequences on diagnosis of cystic fibrosis mutations. The Journal of Molecular Diagnostics 11(5): 488-493.
Friedman et al., (1999) Correction of aberrant splicing of the cystic fibrosis transmembrane conductance regulator (CFTR) gene by antisense oligonucleotides. J Biol Chem 274(51): 36193-36199.
Gebski et al., (2003) Morpholino antisense oligonucleotide induced dystrophin exon 23 skipping in mdx mouse muscle. Hum Mol Genet 12(15): 1801-1811.
Goemans et al., (2011) Systemic administration of PRO051 in Duchenne's muscular dystrophy. N Engl J Med 364 (16): 1513-1522.
Goyenvalle et al., (2010) Prevention of dystrophic pathology in severely affected dystrophin/utrophin-deficient mice by morpholino-oligomer-mediated exon-skipping. Mol Ther 18(1): 198-205.
Groman et al., (2004) Variation in a repeat sequence determines whether a common variant of the cystic fibrosis transmembrane conductance regulator gene is pathogenic or benign. Am J Hum Genet 74(1): 176-179.
Hammond et al., (2011) Genetic therapies for RNA mis-splicing diseases. Trends Genet 27(5): 196-205.
Hefferon et al., (2002) Atypical 5' splice sites cause CFTR exon 9 to be vulnerable to skipping. Am J Hum Genet 71(2): 294-303.
Hefferon et al., (2004) A variable dinucleotide repeat in the CFTR gene contributes to phenotype diversity by forming RNA secondary structures that alter splicing. Proc Natl Acad Sci U S A 101(10): 3504-3509.
Hua et al., (2010) Antisense correction of SMN2 splicing in the CNS rescues necrosis in a type III SMA mouse model. Genes Dev 24(15): 1634-1644.
Kerem et al., (1990) Identification of mutations in regions corresponding to the two putative nucleotide (ATP)-binding folds of the cystic fibrosis gene. Proc Natl Acad Sci U S A 87(21): 8447-8451.
Kerem et al., (1997) A missense cystic fibrosis transmembrane conductance regulator mutation with variable phenotype. Pediatrics 100(3): E5.
Kiesewetter et al., (1993) A mutation in CFTR produces different phenotypes depending on chromosomal background. Nat Genet 5(3): 274-278.
Kinali et al., (2009) Local restoration of dystrophin expression with the morpholino oligomer AVI-4658 in Duchenne muscular dystrophy: a single-blind, placebo-controlled, dose-escalation, proof-of-concept study. Lancet Neurol 8(10): 918-928.
King et al., (2000) R-domain interactions with distal regions of CFTR lead to phosphorylation and activation. Biochemistry 39(32): 9868-9875.
Liu et al., (2002) Partial correction of endogenous DeltaF508 CFTR in human cystic fibrosis airway epithelia by spliceosome-mediated RNA trans-splicing. Nat Biotechnol 20(1): 47-52.
Lorson et al., (2010) Spinal muscular atrophy: mechanisms and therapeutic strategies. Hum Mol Genet 19(R1): R111-R118.
Lu et al., (2011) The status of exon skipping as a therapeutic approach to duchenne muscular dystrophy. Mol Ther 19(1): 9-15.
Lubamba et al., (2012) Cystic fibrosis: insight into CFTR pathophysiology and pharmacotherapy. Clin Biochem 45(15): 1132-1144.
Mann et al., (2001) Antisense-induced exon skipping and synthesis of dystrophin in the mdx mouse. Proc Natl Acad Sci U S A 98(1): 42-47.
Hinrichs et al., (2006) The UCSC Genome Browser Database: update 2006. Nucleic Acids Res 34(Database issue): D590-0598.

* cited by examiner attgaaatatctgacaactcatctttatttgatgtgtgtgtgtgtgtttaacagGGATT
TGGGGAATTATTTGAGAAAGCAAAACAAAACAATAACAATAGAAAAACTT
CTAATGGTGATGACAGCCTCTTCTTCAGTAATTTCTCACTTCTTGGTACT
CCTGTCCTGAAAGATATTAATTTCAAGATAGAAAGGACAGTTGTTGG
CGGTTGCTGGATCCACTGGAGCAGGCAAGgtagttctttgttcttcactattaagaact
taatttggtgtccatgtctcttttttctagtttgtagtgctggaagg (SEQ ID NO: 27)

FIGURE 2

SEQUENCE LISTING

```
<160> NUMBER OF SEQ ID NOS: 28

<210> SEQ ID NO 1
<211> LENGTH: 6132
<212> TYPE: RNA
<213> ORGANISM: Homo sapiens

<400> SEQUENCE: 1
aauuggaagc aaaugacauc acagcagguc agagaaaaag gguugagcgg caggcaccca      60
gaguaguagg ucuuuggcau uaggagcuug agcccagacg gcccuagcag ggaccccagc     120
gcccgagaga ccaugcagag gucgccucug gaaaaggcca gcguugucuc caaacuuuuu     180
uucagcugga ccagaccaau uuugaggaaa ggauacagac agcgccugga auugucagac     240
auauaccaaa ucccuucugu ugauucugcu gacaaucuau cugaaaaauu ggaaagagaa     300
ugggauagag agcuggcuuc aaagaaaaau ccuaaacuca uuaaugcccu ucggcgaugu     360
uuuuucugga gauuuauguu cuauggaauc uuuuuauauu uaggggaagu caccaaagca     420
guacagccuc ucuuacuggg aagaaucaua gcuuccuaug acccggauaa caaggaggaa     480
cgcucuaucg cgauuuaucu aggcauaggc uuaugccuuc ucuuuauugu gaggacacug     540
cuccuacacc cagccauuuu uggccuucau cacauuggaa ugcagaugag aauagcuaug     600
uuuaguuuga uuuauaagaa gacuuuaaag cugucaagcc guguucuaga uaaaauaagu     660 auggacaac uuguuagucu ccuuuccaac aaccugaaca aauuugauga aggacuugca     720
uuggcacauu ucgugugau cgcuccuuug caagugcac uccucauggg gcuaaucugg     780
gaguuguuac aggcgucugc cuucugugga cuugguuucc ugauaguccu ugcccuuuuu     840
caggcugggc uagggagaau gaugaugaag uacagagauc agagagcugg gaagaucagu     900
gaaagacuug ugauuaccuc agaaaugauu gaaaauaucc aaucuguuaa ggcauacugc     960
ugggaagaag caauggaaaa aaugauugaa aacuuaagac aaacagaacu gaaacugacu    1020
cggaaggcag ccuaugugag auacuucaau agcucagccu ucuucuucuc aggguucuuu    1080
gugguguuuu uaucugugcu ucccuaugca cuaaucaaag gaaucauccu ccggaaaaua    1140
uucaccacca ucucauucug cauuguucug cgcauggcgg ucacucggca auuucccugg    1200
gcuguacaaa caugguauga cucucuugga gcaauaaaca aaauacagga uuucuuacaa    1260
aagcaagaau auaagacauu ggaauauaac uuaacgacua cagaaguagu gauggagaau    1320
guaacagccu ucugggagga gggauuuggg aauuauuug agaaagcaaa acaaaacaau    1380
aacaauagaa aaacuucuaa uggugaugac agccucuucu ucaguaauuu cucacuucuu    1440
gguacuccug uccugaaaga uauuaauuuc aagauagaaa gaggacaguu guggcgguu    1500 gcuggauucca cuggagcagg caagacuuca cuucuaaugg ugauuauggg agaacuggag    1560
ccuucagagg guaaaauuaa gcacagugga agaauuucau ucuguucuca guuuccugg    1620 auuaugcug gcaccauuaa agaaaauauc aucuuggug uuuccuauga ugaauauaga    1680
```

-continued

```
uacagaagcg ucaucaaagc augccaacua gaagaggaca ucuccaaguu ugcagagaaa    1740
gacaauauag uucuuggaga agguggaauc acacugagug gaggucaacg agcaagaauu    1800
ucuuuagcaa gagcaguaua caaagaugcu gauuuguauu uauuagacuc uccuuuugga    1860
uaccuagaug uuuuaacaga aaaagaaaua uuugaaagcu gugucuguaa acugauggcu    1920
aacaaaacua ggauuuuggu cacuucuaaa auggaacauu aaagaaagc ugacaaaaua     1980 uuaauuuugc augaagguag cagcauauuu uaugggacau uuucagaacu ccaaaaucua    2040
cagccagacu uuagcucaaa acucauggga ugugauucuu cgaccaauu uagugcagaa     2100 agaagaaauu caauccuaac ugagaccuua caccguuucu cauuagaagg agaugcuccu    2160
gucuccugga cagaaacaaa aaaacaaucu uuuaaacaga cuggagaguu uggggaaaaa    2220
aggaagaauu cuauucucaa uccaaucaac ucuaucgaa aauuuuccau gugcaaaag      2280 acucccuuac aaaugaaugg caucgaagag gauucugaug agccuuuaga gagaaggcug    2340
uccuuaguac cagauucuga gcagggagag gcgauacugc ucgcaucag cgugaucagc     2400 acuggccca cgcuucaggc acgaaggagg cagucugucc ugaaccugau gacacacuca     2460
guuaaccaag gucagaacau ucaccgaaag acaacagcau ccacgaaaa agugucacug     2520 gccccucagg caaacuugac ugaacuggau auauauucaa gaagguuauc ucaagaaacu    2580
ggcuuggaaa uagugaaga aauuaacgaa gaagacuuaa aggagugcuu uuugaugau      2640 auggagagca uaccagcagu gacuacaugg aacacauacc uucgauauau uacuguccac    2700
aagagcuuaa uuuuugugcu aauuuggugc uuaguaauuu ucucggcaga gguggcugcu    2760
ucuuuggutg ugcugugggcu ccuuggaaac acuccucuuc aagacaaagg gaauaguacu   2820
cauaguagaa auaacagcua ugcagugauu ucaccagca ccaguucgua uuaugugu       2880 uacauuuacg ugggaguagc cgacacuuug cuugcuaugg gauucuucag aggcuacca     2940 cuggugcaua ucuuaucac agugucgaaa auuuuacacc acaaaauguu acauucuguu     3000
cuucaagcac cuaugucaac cccuaacacg uugaaagcag gugggauucu aauagauuc     3060 uccaaagaua uagcaauuuu ggaugaccuu cugccucuua ccauauuuga cuucauccag    3120
uuguuauuaa uugugauugg agcuauagca guugucgcag uuuuacaacc cuacaucuuu    3180
guugcaacag ugccagugau aguggcuuuu auuauguuga gagcauauuu ccuccaaacc    3240
ucacagcaac ucaaacaacu ggaaucgaa ggcaggaguc caauuuucac ucaucuuguu     3300
acaagcuuaa aaggacuaug gacacuucgu gccuucggac ggcagccuua cuuugaaacu    3360 cuguccaca aagcucugaa uuuacauacu gccaacuggu ucuuguaccu gucaacacug    3420
cgcugguucc aaaugagaau agaaaugauu uugucaucu cuucauugc uguuaccuuc     3480 auuccauuu uaacaacagg agaaggagaa ggaagaguug uauuauccu gacuuuagcc     3540 augaauauca ugaguacauu gcagugggcu guaaacucca gcauagaugu ggauagcuug    3600
augcgaucug ugagccgagu cuuuaaguuc auugacaugc caacagaagg uaaaccuacc    3660
aagucaacca aaccauacaa gaauggccaa cucucgaaag uuaugauuau ugagaauuca    3720
cacgugaaga aagaugacau cuggcccuca gggggccaaa ugacugucaa agaucucaca    3780
gcaaaauaca cagaaggugg aaaugccaua uuagagaaca uuccuucuc aauaagccuu    3840 ggccagaggg uggaccucuu gggaagaacu ggaucaggga agaguacuuu guuaucagcu   3900 uuuugagac uacugaacac ugaaggagaa auccagaucg auggugguguc uugggauuca    3960 auaacuuugc aacaguggag gaaagccuuu ggagugauac cacagaaagu auuuauuuu     4020 ucuggaacau uuagaaaaaa cuuggauccc uaugaacagu ggagugauca agaaauaugg    4080
```

```
aaaguugcag augagguugg gcucagaucu gugauagaac aguuccugg gaagcuugac    4140 uuugaccuug uggauggggg cuguguccua agccauggcc acaagcaguu gaugugcuug    4200
gcuagaucug uucucaguaa ggcgaagauc uugcugcuug augaacccag ugcucauuug    4260
gauccaguaa cauaccaaau aauuagaaga acucuaaaac aagcauuugc ugauugcaca    4320
guaauucucu gugaacacag gaugaagca augcuggaau gccaacaauu uuggucaua     4380 gaagagaaca aagugcggca guacgauucc auccagaaac ugcugaacga gaggagccuc    4440
uuccggcaag ccaucagccc cuccgacagg gugaagcucu uccccaccg gaacucaagc     4500 aagugcaagu cuaagcccca gauugcugcu cugaaagagg agacagaaga agaggugcaa    4560
gauacaaggc uuuagagagc agcauaaaug uugacauggg acauuugcuc auggaauugg    4620
agcucguggg acagucaccu cauggaauug gagcucgugg aacaguuacc ucugccucag    4680
aaaacaagga ugaauuaagu uuuuuuuuaa aaaagaaaca uuugguaagg ggaauugagg    4740
acacugauau gggucuugau aaauggcuuc cuggcaauag ucaaauugug ugaaagguac    4800
uucaaauccu ugaagauuua ccacuugugu uuugcaagcc agauuuuccu gaaaacccuu    4860
gccaugugcu aguaauugga aaggcagcuc uaaaugucaa ucagccuagu gaucagcuu     4920 auugucuagu gaaacucguu aauuuguagu guuggagaag aacugaaauc auacuucuua    4980
ggguuaugau uaaguaauga uaacuggaaa cuucagcggu uuauauaagc uuguauuccu    5040
uuuucucucc ucuccccaug auguuuagaa acacaacuau auuguuugcu aagcauucca    5100
acuaucucau uuccaagcaa guauuagaau accacaggaa ccacaagacu gcacaucaaa    5160
auaugcccca uucaacaucu agugagcagu caggaaagag aacuuccaga uccuggaaau    5220
caggguuagu auuguccagg ucuaccaaaa aucucaauau uucagauaau cacaauacau    5280
cccuuaccug ggaaagggcu guuauaaucu uucacagggg acaggauggu ucccuugaug    5340
aagaaguuga uaugccuuuu cccaacucca gaaagugaca agcucacaga ccuuugaacu    5400
agaguuuagc uggaaaagua uguuagugca aauugucaca ggacagcccu ucuuuccaca    5460
gaagcuccag guagagggug uguaaguaga uaggccaugg gcacguggg uagacacaca     5520 ugaaguccaa gcauuuagau guauagguug augguggau guuucaggc uagauguaug       5580 uacuucaugc ugucuacacu aagagagaau gagagacaca cugaagaagc accaaucaug    5640
aauuaguuuu auaugcuucu guuuuauaau uuugugaagc aaaauuuuuu cucuaggaaa    5700
uauuuauuuu aauaaugaau caaacauaua uaacaaugcu guauuuaaaa agaaugauua    5760
ugaauuacau uuguauaaaa uaauuuuuau auuugaaaua uugacuuuuu auggcacuag    5820
uauuucuaug aaauauuaug uuaaaacugg acaggggag aaccuagggu gauauuaacc     5880 agggccaug aaucaccuuu uggucuggag ggaagccuug gggcugaugc aguuguugcc     5940
cacagcugua ugauucccag ccagcacagc cucuuagaug caguucugaa gaagauggua    6000
ccaccagucu gacuguuucc aucaagggua cacugccuuc ucaacuccaa acugacucuu    6060
aagaagacug cauuauauuu auuacuguaa gaaaauauca cuugucaaua aaauccauac    6120
auuuguguga aa                                                       6132
```

<210> SEQ ID NO 2
<211> LENGTH: 983
<212> TYPE: RNA
<213> ORGANISM: Homo sapiens

<400> SEQUENCE: 2

```
cagcuuugaa agaggaggau uauaaaaucu aucucauguu aaugcugaag auuaaauaau      60
aguguuuaug uaccccgcuu auaggagaag agggugugug ugugugugug ugugugugug     120
uguguaugug uauguauaca uguauguauu cagucuuuac ugaaauuaaa aaaucuuuaa     180
cuugauaaug ggcaaauauc uuaguuuuag aucauguccu cuagaaaccg uaugcuauau     240
aauuauguac uauaaaguaa uaauguauac aguguaaugg aucaugggcc augugcuuuu     300
caaacuaauu guacauaaaa caagcaucua uugaaaauau cugacaaacu caucuuuuau     360 uuugauguguu ugugugugug ugugugugugu uuuuuaacag ggauuggggg aauuauuuga    420
gaaagcaaaa caaaacaaua acaauagaaa aacuucuaau ggugaugaca gccucuucuu     480
caguaauuuc ucacuucuug guacuccugu ccugaaagau auuaauuuca agauagaaag     540
aggacaguug uuggcgguug cuggauccac uggagcaggc aagguaguuc uuuuguucuu     600
cacuauuaag aacuuaauuu ggugucc aug ucucuuuuuu uuucuaguuu guagugcugg     660
aagguauuuu uggagaaauu cuuacaugag cauuaggaga auguauggu guagugcuuu      720 guauaauaga aauuguucca cugauaauuu acucuaguuu uuuauuuccu cauauuauuu     780
ucaguggcuu uuucuuccac aucuuuauau uuugcaccac auucaacacu guaucuugca     840
cauggcgagc auucaauaac uuuauugauu aaacaaauca uccauuuuau ccaucuuaa      900 ccagaacaga cauuuuuuca gagcugguccc aggaaaauca ugacuuacau uuugccuuag    960
uaaccacaua aacaaaaggu cuc                                             983

<210> SEQ ID NO 3
<211> LENGTH: 122
<212> TYPE: RNA
<213> ORGANISM: Homo sapiens

<400> SEQUENCE: 3
uuguggaucu aaauuucagu ugacuuguca ucuugauuuc uggagaccac aagguaauga      60
aaaauaauua caagagucuu ccaucuguug caguauuaaa auggcgagua agacacccug     120
aa                                                                    122

<210> SEQ ID NO 4
<211> LENGTH: 132
<212> TYPE: RNA
<213> ORGANISM: Homo sapiens

<400> SEQUENCE: 4
ucaccuugug gaucuaaauu ucaguugacu ugcaucuug auuucuggag accacaaggu       60
aaugaaaaau aauuacaaga gucuuccauc uguugcagua uuaaauggc gaguaagaca      120 cccugaaagg aa                                                         132

<210> SEQ ID NO 5
<211> LENGTH: 84
<212> TYPE: RNA
<213> ORGANISM: Homo sapiens

<400> SEQUENCE: 5
uugacuuguc aucugauuuu cuggagacca caagguaaug aaaaauaauu acaagagucu      60
uccaucuguu gcaguauuaa aaug                                            84

<210> SEQ ID NO 6
<211> LENGTH: 25
<212> TYPE: RNA
<213> ORGANISM: Artificial Sequence
```

```
<220> FEATURE:
<223> OTHER INFORMATION: Antisense Oligonucleotide

<400> SEQUENCE: 6
aaaucaagau gacaagucaa cugaa                                              25

<210> SEQ ID NO 7
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 7
cuuguggucu ccagaaauca agaug                                              25

<210> SEQ ID NO 8
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 8
aacagaugga agacucuugu aauua                                              25

<210> SEQ ID NO 9
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 9 ucagggguguc uuacucacca uuuua                                             25

<210> SEQ ID NO 10
<211> LENGTH: 22
<212> TYPE: RNA
<213> ORGANISM: Artificial Sequence
<220> FEATURE:
<223> OTHER INFORMATION: Antisense Oligonucleotide

<400> SEQUENCE: 10
cuagaaaaaa aaagagacau gg                                                 22

<210> SEQ ID NO 11
<211> LENGTH: 6216
<212> TYPE: RNA
<213> ORGANISM: Homo sapiens

<400> SEQUENCE: 11
aauuggaagc aaaugacauc acagcagguc agagaaaaag gguugagcgg caggcacccc        60
gaguaguagg ucuuuggcau uaggagcuug agcccagacg gcccuagcag ggaccccagc       120
gcccgagaga ccaugcagag gucgccucug gaaaaggcca gcguugucuc caaacuuuuu       180
uucagcugga ccagaccaau uuugaggaaa ggauacagac agcgccugga auugucagac       240
auauaccaaa ucccuucugu ugauucugcu gacaaucuau cugaaaaauu ggaaagagaa       300
ugggauagag agcuggcuuc aaagaaaaau ccuaaacuca uuaaugcccu ucggcgaugu       360
uuuuucugga gauuuauguu cuauggaauc uuuuuauauu uaggggaagu caccaaagca       420
guacagccuc ucuuacuggg aagaaucaua gcuuccuaug acccggauaa caaggaggaa       480
```

| | | | | | |
|---|---|---|---|---|---|
| cgcucuaucg | cgauuuaucu | aggcauaggc | uuaugccuuc | ucuuuauugu | gaggacacug | 540 |
| cuccuacacc | cagccauuuu | uggccuucau | cacauuggaa | ugcagaugag | aauagcuaug | 600 |
| uuuaguuuga | uuuauaagaa | gacuuuaaag | cugucaagcc | guguucuaga | uaaaauaagu | 660 |
| auuggacaac | uuguuagucu | ccuuuccaac | aaccugaaca | aauuugauga | aggacuugca | 720 |
| uuggcacauu | ucguguggau | cgcuccuuug | caaguggcac | uccucauggg | gcuaaucugg | 780 |
| gaguuguuac | aggcgucugc | cuucugugga | cuugguuucc | ugauaguccu | ugcccuuuuu | 840 |
| caggcugggc | uagggagaau | gaugaugaag | uacagagauc | agagagcugg | gaagaucagu | 900 |
| gaaagacuug | ugauuaccuc | agaaaugauu | gaaaauaucc | aaucuguuaa | ggcauacugc | 960 |
| ugggaagaag | caauggaaaa | aaugauugaa | aacuuaagac | aaacagaacu | gaaacugacu | 1020 |
| cggaaggcag | ccuaugugag | auacuucaau | agcucagccu | ucuucuucuc | agggucuuu | 1080 |
| guggugaauu | uaucugugcu | ucccuaugca | cuaaucaaag | gaaucauccu | ccggaaaaua | 1140 |
| uucaccacca | ucucauucug | cauuguucug | cgcauggcgg | ucacucggca | auuucccugg | 1200 |
| gcuguacaaa | cauggauga | cucucuugga | gcaauaaaca | aaaucagga | uuucuuacaa | 1260 |
| aagcaagaau | auaagacauu | ggaauauaaac | uuaacgacua | cagaaguagu | gauggagaau | 1320 |
| guaacagccu | ucggggagga | gggauuuggg | gaauuauuug | agaaagcaaa | acaaaacaau | 1380 |
| aacaauagaa | aaacuucuaa | uggugaugac | agccucuucu | ucaguaauuu | cucacuucuu | 1440 |
| gguacuccug | uccugaaaga | uauuaauuuc | aagauagaaa | gaggacaguu | guuggcgguu | 1500 |
| gcuggaucca | cuggagcagg | caagacuuca | cuucuaaugg | ugauuauggg | agaacuggag | 1560 |
| ccuucagagg | guaaaauuaa | gcacaguggg | agaauuucau | ucuguucuca | guuuccugg | 1620 |
| auuaugccug | gcaccauuaa | agaaaauauc | aucuuggug | uuccuauga | ugaauauaga | 1680 |
| uacagaagcg | ucaucaaagc | augccaacua | gaagaggaca | ucuccaaguu | ugcagagaaa | 1740 |
| gacaauauag | uucuuggaga | aggugaauc | acacugagug | gaggucaacg | agcaagaauu | 1800 |
| ucuuuagcaa | gagcaguaua | caaagaugcu | gauuugauu | uauuagcuc | uccuuuugga | 1860 |
| uaccuagaug | uuuuaacaga | aaaagaaaua | uuugaaagcu | gugucuguaa | acugauggcu | 1920 |
| aacaaaacua | ggauuuuggu | cacuucaaaa | auggaacauu | uaagaaagc | ugacaaaaua | 1980 |
| uuaauuuugc | augaagguag | cagcuauuuu | uaugggacau | uucagaaacu | ccaaaaucua | 2040 |
| cagccagacu | uuagcucaaa | acucauggga | ugugauucuu | ucgaccaauu | uagugcagaa | 2100 |
| agaagaaauu | caauccuaac | ugagaccuua | caccguuucu | cauuagaagg | agaugcuccu | 2160 |
| gucuccugga | cagaaacaaa | aaaacaaucu | uuuaaacaga | cuggagaguu | uggggaaaaa | 2220 |
| aggaagaauu | cuauucucaa | uccaaucaac | ucuauacgaa | aauuuccau | ugugcaaaag | 2280 |
| acucccuuac | aaaugaaugg | caucgaagag | gauucgaug | agccuuuaga | gagaaggcug | 2340 |
| uccuuaguac | cagauucuga | gcagggagag | gcgauacugc | cucgcaucag | cgugaucagc | 2400 |
| acuggcccca | cgcuucaggc | acgaaggagg | cagucuguc | ugaaccugau | gacacacuca | 2460 |
| guuaaccaag | gucagaacau | ucaccgaaag | acaacagcau | ccacacgaaa | agugucacug | 2520 |
| gcccucagg | caaacuugac | ugaacuggau | auauauucaa | gaagguuauc | ucaagaaacu | 2580 |
| ggcuuggaaa | uaguaagaga | aauuaacgaa | gaagacuuaa | aggagugcuu | uuugaugau | 2640 |
| auggagagca | uaccagcagu | gacuacaugg | aacacauacc | uucgauauau | uacuguccac | 2700 |
| aagagcuuaa | uuuuugugcu | aauuggguc | uuaguaauuu | ucuggcaga | gguggcugcu | 2760 |
| ucuuugguug | ugcugugggcu | ccuuggaaac | acuccucuuc | aagacaaagg | gaauagaacu | 2820 |
| cauaguagaa | auaacagcua | ugcagugauu | auccaccagca | ccaguucgua | uuauguguuu | 2880 |

```
uacauuuacg ugggaguagc cgacacuuug cuugcuaugg gauucuucag aggucuacca   2940
cuggugcaua cucuaaucac agugucgaaa auuuuacacc acaaaauguu acauucuguu   3000
cuucaagcac cuaugucaac ccucaacacg uugaaagcag gugggauucu uaauagauuc   3060
uccaaagaua uagcaauuuu ggaugaccuu cugccucuua ccauauuuga cuucauccag   3120
uuguuauuaa ugugauugg agcauagca guugucgcag uuuuacaacc cuacaucuuu   3180
guugcaacag ugccagugau aguggcuuuu auuauguuga gagcauauuu ccuccaaacc   3240
ucacagcaac ucaaacaacu ggaaucugaa ggcaggaguc caauuuucac ucaucuuguu   3300
acaagcuuaa aaggacuaug gacacuucgu gccuucggac ggcagccuua cuugaaaacu   3360
cguuccaca aagcucugaa uuuacauacu gccaacuggu ucuuguaccu gucaacacug   3420
cgcugguucc aaaugagaau agaaaugauu uuugucaucu ucuucauugc guuaccuuc   3480
auuuccauuu uaacaacagg agaaggagaa ggaagaguug uauuauccu gacuuuagcc   3540
augaauauca ugaguacauu gcagggggcu guaaacucca gcauagaugu ggauagcuug   3600
augcgaucug ugagccgagu cuuuaaguuc auugacaugc caacagaagg uaaaccuacc   3660
aagucaacca aaccauacaa gaauggccaa cucucgaaag uuaugauuau ugagaauuca   3720
cacgugaaga aagaugacau cuggcccuca ggggccaaa ugacugucaa agaucucaca   3780
gcaaaauaca cagaaggugg aaaugccaua uuagagaaca uuccuucuc aauaaguccu   3840
ggccagaggu ugacuuguca ucuugauuuc uggagaccac aagguaauga aaauaauua   3900
caagagucuu ccaucuguug caguauuaaa augguggggcc ucuugggaag aacuggauca   3960
gggaagagua cuuuguuauc agcuuuuug agacuacuga acacugaagg agaaauccag   4020
aucgauggug ugucuuggga uucaauaacu ugcaacagu ggaggaaagc cuuuggagug   4080
auaccacaga aaguauuuau uuuuucugga acauuuagaa aaaacuugga ucccuaugaa   4140
caguggagug aucaagaaau auggaaaguu gcagaugagg uugggcucag aucugugaua   4200
gaacaguuuc cugggaagcu ugacuuuguc cuuguggaug ggggcugugu ccuaagccau   4260
ggccacaagc aguugaugug cuggcuaga ucuguucuca guaaggcgaa gaucuugcug   4320
cuugaugaac ccagugcuca uuuggaucca guaacauacc aaauaauuag aagaacucua   4380
aaacaagcau uugcugauug cacaguaauu cucugugaac acaggauaga agcaaugcug   4440
gaaugccaac aauuuuuggu cauagaagag aacaaagugc ggcaguacga uuccauccag   4500
aaacugcuga acgagaggag ccucuuccgg caagccauca gccccuccga cagggugaag   4560
cucuuuccc accggaacuc aagcaagugc aagucaagc cccagauugc ugcucugaaa   4620
gaggagacag aagaagaggu gcaagauaca aggcuuuaga gagcagcaua aauguugaca   4680
ugggacauuu gcucauggaa uuggagcucg ugggacaguc accucaugga auuggagcuc   4740
guggaacagu uaccucugcc ucagaaaaca aggaugaauu aaguuuuuu uuaaaaaga   4800
aacauuuggu aaggggaauu gaggacacug auaugggucu ugauaaaugg cuccuggca   4860
auagucaaau ugugugaaag guacuucaaa uccuugaaga uuuaccacuu uguuuugca   4920
agccagauuu uccugaaaac ccuugccaug ugcuaguaau uggaaaggca gcucuaaaug   4980
ucaaucagcc uaguugauca gcuuauuguc uaguaaacu cguuaauuug uaguguuuga   5040
gaagaacuga aaucauacuu cuuaggguua ugauuaagua augauaacug gaaacuucag   5100
cgguuuauau aagcuuguau uccuuuucu cuccucuccc caugauguuu agaaacacaa   5160
cuauauuguu ugcuaagcau uccaacuauc ucauuuccaa gcaaguauua gaauaccaca   5220
```

| | | |
|---|---|---|
| ggaaccacaa gacugcacau caaaauaugc cccauucaac aucuagugag cagucaggaa | 5280 | |
| agagaacuuc cagauccugg aaaucagggu uaguauuguc caggucuacc aaaaaucuca | 5340 | |
| auauuucaga uaaucacaau acaucccuua ccugggaaag ggcuguuaua aucuuucaca | 5400 | |
| ggggacagga ugguucccuu gaugaagaag uugauaugcc uuuucccaac uccagaaagu | 5460 | |
| gacaagcuca cagaccuuug aacuagaguu uagcuggaaa aguauguuag ugcaaauugu | 5520 | |
| cacaggacag cccuucuuuc cacagaagcu ccagguagag ggugnguaag uagauaggcc | 5580 | |
| augggcacug ugggnuagaca cacaugaagu ccaagcauuu agauguauag guugauggug | 5640 | |
| guauguuuuc aggcuagaug uauguacuuc augcugucua cacuaagaga gaaugagaga | 5700 | |
| cacacugaag aagcaccaau caugaauuag uuuuauaugc uucuguuuua uaauuuugug | 5760 | |
| aagcaaaauu uuuucucuag gaaauauuua uuuuaauaau guuucaaaca uauauaacaa | 5820 | |
| ugcuguauuu uaaaagaaug auuaugaauu acauuuguau aaaauaauuu uuauauuuga | 5880 | |
| aauauugacu uuuuauggca cuaguauuuc uaugaaauau uauguuaaaa cuggacagg | 5940 | |
| ggagaaccua gggugauauu aaccaggggc caugaaucac cuuuuggucu ggagggaagc | 6000 | |
| cuuggggcug augcaguugu ugcccacagc uguaugauuc ccagccagca cagcccucuua | 6060 | |
| gaugcaguuc ugaagaagau gguaccacca gucgacugu uccaucaag gguacacugc | 6120 | |
| cuucucaacu ccaaacugac ucuuaagaag acugcauuau auuuauuacu guaagaaaau | 6180 | |
| aucacuuguc aauaaaaucc auacauuugu gugaaa | 6216 | |

<210> SEQ ID NO 12
<211> LENGTH: 5949
<212> TYPE: RNA
<213> ORGANISM: Homo sapiens

<400> SEQUENCE: 12

| | | |
|---|---|---|
| aauuggaagc aaaugacauc acagcagguc agagaaaaag gguugagcgg caggcaccca | 60 | |
| gaguaguagg ucuuuggcau uaggagcuug agcccagacg gcccuagcag ggaccccagc | 120 | |
| gcccgagaga ccaugcagag gucgccucug gaaaaggcca gcguugucuc caaacuuuuu | 180 | |
| uucagcugga ccagaccaau uuugaggaaa ggauacagac agcgccugga auugucagac | 240 | |
| auauaccaaa ucccuucugu ugauucugcu gacaaucuau cugaaaaauu ggaaagagaa | 300 | |
| ugggauagag agcuggcuuc aaagaaaaau ccuaaacuca uuaaugcccu ucggcgaugu | 360 | |
| uuuuucugga gauuuauguu cuauggaauc uuuuuauauu uaggggaagu caccaaagca | 420 | |
| guacagccuc ucuuacuggg aagaaucaua gcuuccuaug acccggauaa caaggaggaa | 480 | |
| cgcucuaucg cgauuuaucu aggcauaggc uuaugccuuc ucuuuauugu gaggacacug | 540 | |
| cuccuacacc cagccauuuu uggccuucau cacauuggaa ugcagaugag aauagcuaug | 600 | |
| uuuaguuuga uuuauaagaa acuuuaaag cugucaagcc guuucuaga uaaaauaagu | 660 | |
| auuggacaac uuguuagucu ccuuuccaac aaccgaaca aauuugauga aggacuugca | 720 | |
| uuggcacauu ucguguggau cgcuccuuug caaguggcac uccucauggg gcuaaucugg | 780 | |
| gaguuguuac aggcgucugc cuucugugga cuggunuuccc ugauaguccu ugcccuuuuu | 840 | |
| caggcugggc uagggagaau gaugaugaag uacagagauc agagagcugg gaagaucagu | 900 | |
| gaaagacuug ugauuaccuc agaaaugauu gaaauauucc aaucuguuaa ggcauacugc | 960 | |
| ugggaagaag caauggaaaa aaugauugaa acuuaagac aaacagaacu gaaacugacu | 1020 | |
| cggaaggcag ccuaugugag auacuucaau agcucagccu ucuucuucuc aggguucuuu | 1080 | |
| gugguguuuu uaucugugcu ucccuaugca cuaaucaaag gaaucauccu ccggaaaaua | 1140 | |

```
uucaccacca ucucauucug cauuguucug cgcauggcgg ucacucggca auucccugg     1200 gcuguacaaa cauggauga cucucuugga gcaauaaaca aaauacagga uuucuuacaa     1260
aagcaagaau auaagacauu ggaauauaac uuaacgacua cagaaguagu gauggagaau   1320
guaacagccu ucugggagga gacuucacuu cuaauggguga uuaugggaga acuggagccu   1380
ucagagggua aaauuaagca caguggaaga auucauucu guucucaguu uccuggauu      1440 augccuggca ccauuaaaga aaauaucauc uuuggguguu ccaugauga auauagauac     1500 agaagcguca ucaaagcaug ccaacuagaa gaggacaucu ccaaguuugc agagaaagac    1560
aauauaguuc uuggagaagg uggaaucaca cugaguggag gucaacgagc aagaauuucu    1620
uuagcaagag caguauacaa agaugcugau uuguauuuau uagacucucc uuuuggauac    1680
cuagauguuu uaacagaaaa agaaauauuu gaaagcugug ucuguaaacu gauggcuaac    1740
aaaacuagga uuuggucac uucuaaaaug gaacauuuaa agaaagcuga caaaauauua     1800
auuuugcaug aaguagcag cuauuuuuau gggacauuuu cagaacucca aaucuacag     1860 ccagacuuua gcucaaaacu caugggaugu gauucuuucg accaauuuag gcagaaaaga    1920
agaaauucaa uccaacuga gaccuuacac cguuucucau uagaaggaga ugcuccuguc     1980 uccggacag aaacaaaaaa acaaucuuuu aaacagacug gagaguuugg ggaaaaaagg    2040
aagaauucua uucucaaucc aaucaacucu auacgaaaau uuccauugu gcaaaagacu     2100 cccuuacaaa ugaauggcau cgaagaggau ucgaugagc cuuuagagag aaggcuguccc   2160 uuaguaccag auucugagca gggagaggcg auacugccuc gcaucagcgu gaucagcacu   2220
ggccccacgc uucaggcacg aaggaggcag ucuguccuga accugaugac acacucaguu   2280
aaccaagguc agaacauuca ccgaaagaca acagcauccaa cacgaaaagu gucacuggcc  2340
ccucaggcaa acuugacuga acuggauaua uauucaagaa gguuaucuca agaaacuggc    2400
uuggaaauaa gugaagaaau uaacgaagaa gacuuaaagg agugcuuuuu ugaugauaug   2460
gagagcauac cagcagugac uacauggaac acauaccuuc gauauauuac ugucccacaag  2520 agcuuaauuu uugugcuaau uuggugcuua guauuuuuuc uggcagaggu ggcugcuucu    2580
uugguugugc uguggcuccu uggaaacacu ccucuucaag acaaagggaa uaguaccau     2640 aguagaaaua acagcuaugc agugauuauc accagcacca guucguauua uguguuuac    2700 auuuacgugg gaguagccga cacuuugcuu gcuaugggau ucuucagagg ucuaccacug   2760
gugcauacuc uaaucacagu gucgaaaau uuacaccaca aaauguuaca uucguucuu     2820 caagcaccua ugucaacccu caacacguug aaagcaggug ggauucuuaa uagauucucc    2880 aaagauaug caauuuugga ugaccucug ccucuuacca uauugacuu cauccaguug    2940 uuauuaauug ugauuggagc uauagcaguu gucgcaguuu acaacccua caucuuugu     3000 gcaacagugc cagugauagu ggcuuuuauu auguugagag cauauuuccu ccaaaccuca    3060
cagcaacuca acaacuugga aucgaaggc aggaguccaa uuucacuca ucuuguuaca     3120 agcuuaaaag gacuauggac acuucgugcc uucggacggc agccuuacuu ugaaacucug   3180
uuccacaaag cucugaauuu acauacgcc aacugguucu uguaccuguc aacacugcgc    3240 ugguccaaa ugaaauaga aaugauuuuu gucaucuucu ucauugcguu uccuucauu      3300 uccauuuuaa caacaggaga aggagaagga agaguuggua uuaccugac uuuagccaug    3360 aauaucauga guacauugca gugggcgua aacccagca uagaugggga uagcuugaug   3420
cgaucuguga gccgagucuu uaaguucauu gacaugccaa cagaagguaa accuaccaag   3480
```

| | |
|---|---|
| ucaaccaaac cauacaagaa uggccaacuc ucgaaaguua ugauuauuga gaauucacac | 3540 |
| gugaagaaag augacaucug gcccucaggg ggccaaauga cugucaaaga ucucacagca | 3600 |
| aaauacacag aaggugggaaa ugccauauua gagaacauuu ccuucucaau aaguccuggc | 3660 |
| cagaggguggg gccucuuggg aagaacugga ucagggaaga guacuuuguu aucagcuuuu | 3720 |
| uugagacuac ugaacacuga aggagaaauc cagaucgaug gugugucuug ggauucaaua | 3780 |
| acuuugcaac aguggaggaa agccuuugga gugauaccac agaaaguauu uauuuuucu | 3840 |
| ggaacauuua gaaaaacuu ggaucccuau gaacaguggaa gugaucaaga aauauggaaa | 3900 |
| guugcagaug agguugggcu cagaucugu auagaacagu uccugggaa gcuugacuuu | 3960 |
| guccuugugg auggggggcug uguccuaagc cauggccaca agcaguugau gugcuuggcu | 4020 |
| agaucuguuc ucaguaaggc gaagaucuug cugcuugaug aacccagugc ucauuuggau | 4080 |
| ccaguaacau accaaauaau uagaagaacu cuaaaacaag cauuugcuga uugcacagua | 4140 |
| auucucugug aacacaggau agaagcaaug cuggaaugcc aacaauuuuu ggucauagaa | 4200 |
| gagaacaaag ugcggcagua cgauuccauc cagaaacugc ugaacgagag gagccucuuc | 4260 |
| cggcaagcca ucagcccccuc cgacaggggug aagcucuuuc cccaccggaa cucaagcaag | 4320 |
| ugcaagucua agccccagau gcugcucug aaagaggaga cagaagaaga ggugcaagau | 4380 |
| acaaggcuuu agagagcagc auaaauguug acaugggaca uuugcucaug gaauuggagc | 4440 |
| ucgugggaca gucaccucau ggaauuggag cucguggaac aguuaccucu gcccagaaa | 4500 |
| acaaggauga auuaaguuuu uuuuuaaaaa agaaacauuu gguaggggga auugaggaca | 4560 |
| cugauauggg ucuugauaaa uggcuuccug gcaauaguca aauguguga aagguacuuc | 4620 |
| aaauccuuga agauuuacca cuugugguuu gcaagccaga uuuuccugaa aacccuugcc | 4680 |
| augugcuagu aauuggaaag gcagcucuaa augucaauca gccuaguuga ucagcuuauu | 4740 |
| gucuagugaa acucguuaau uuguaguguu ggagaagaac ugaaaucaua cuucuuaggg | 4800 |
| uuaugauuaa guaaugauaa cuggaaacuu cagcgguuua uauaagcuug uauuccuuuu | 4860 |
| ucucuccucu ccccaugaug uuuagaaaca caacuauauu guuugcuaag cauccaacu | 4920 |
| aucucauuuc caagcaagua uuagaauacc acaggaacca caagacugca caucaaaaua | 4980 |
| ugccccauuc aacaucuagu gagcagucag gaaagagaac uuccagaucc uggaaaucag | 5040 |
| gguuaguauu guccaggucu accaaaaaauc ucaauauuuc agauaaucac aauacauccc | 5100 |
| uuaccuggga aagggcuguu auaaucuuuc acaggggaca ggauggguucc cuugaugaag | 5160 |
| aaguugauau gccuuuuccc aaccccagaa agugacaagc ucacagaccu uugaacuaga | 5220 |
| guuuagcugg aaaaguaugu uagugcaaau ugucacagga cagcccuucu uuccacagaa | 5280 |
| gcuccaggua gagggugugu aaguagauag gccaugggca cuguggguag acacacauga | 5340 |
| aguccaagca uuuagaugua uaggugaug gugguauguu uucaggcuag auguauguac | 5400 |
| uucaugcugu cuacacuaag agagaauag agacacacug aagaagcacc aaucaugaau | 5460 |
| uaguuuuauua ugcuucuguu uuauaauuuu gugaagcaaa auuuuuucuc uaggaaauau | 5520 |
| uuauuuuaau aauguuucaa acauauauaa caaugcugua uuuuaaaaga augauuauga | 5580 |
| auuacauuug uauaaaauaa uuuuuauauu ugaauauuug acuuuuuaug gcacuaguau | 5640 |
| uucuaugaaa uauuauguua aaacugggac aggggagaaac cuaggguugau auuaaccagg | 5700 |
| ggccaugaau caccuuuugg ucuggaggga agccuuggggg cugaugcagu uguugcccac | 5760 |
| agcuguauga uucccagcca gcacagccuc uuagaugcag uucugaagaa gauggaacca | 5820 |
| ccagucugac uguuccauc aagggguacac ugccuucuca acuccaaacu gacucuuaag | 5880 |

```
aagacugcau uauauuuauu acuguaagaa aauaucacuu gucaauaaaa uccauacauu    5940
ugugugaaa                                                           5949

<210> SEQ ID NO 13
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 13
cuugugaaac uuacugauua ucagg                                         25

<210> SEQ ID NO 14
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 14
ccucuuaccu caguuacaau uuaua                                         25

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
agcatttgct gattgcacag                                               20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
gaaagagctt caccctgtcg                                               20

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
aatgctggaa tgccaacaat t                                             21

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
ggctcctctc gttcagcagt                                               20

<210> SEQ ID NO 19
```

```
<211> LENGTH: 20
<212> TYPE: DNA
<213> ORGANISM: Artificial Sequence
<220> FEATURE:
<223> OTHER INFORMATION: Primer

<400> SEQUENCE: 19
gggccaaatg actgtcaaag                                                     20

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
gcaacagatg gaagactctt gt                                                  22

<210> SEQ ID NO 21
<211> LENGTH: 27
<212> TYPE: DNA
<213> ORGANISM: Artificial Sequence
<220> FEATURE:
<223> OTHER INFORMATION: Primer

<400> SEQUENCE: 21
gccatattag agaacatttc cttctca                                             27

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22
accttgtggt ctccagaaat caa                                                 23

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
ggttctttgt ggtgttttta tc                                                  22

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
gcaataaaca aaatacagga tttc                                                24

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
```

```
aaacttggag atgtcctctt c                                             21

<210> SEQ ID NO 26
<211> LENGTH: 23
<212> TYPE: DNA
<213> ORGANISM: Artificial Sequence
<220> FEATURE:
<223> OTHER INFORMATION: Primer

<400> SEQUENCE: 26
tgctaaagaa attcttgctc gtt                                           23

<210> SEQ ID NO 27
<211> LENGTH: 335
<212> TYPE: DNA
<213> ORGANISM: Homo sapiens

<400> SEQUENCE: 27
attgaaaata tctgacaaac tcatctttta tttttgatgt gtgtgtgtgt gtgtgtgtgt    60 tttttaaca gggatttggg gaattatttg agaaagcaaa acaaaacaat aacaatagaa    120
aaacttctaa tggtgatgac agcctcttct tcagtaattt ctcacttctt ggtactcctg   180
tcctgaaaga tattaatttc aagatagaaa gaggacagtt gttggcggtt gctggatcca   240
ctggagcagg caaggtagtt cttttgttct tcactattaa gaacttaatt tggtgtccat   300
gtctcttttt ttttctagtt tgtagtgctg gaagg                              335

<210> SEQ ID NO 28
<211> LENGTH: 113
<212> TYPE: DNA
<213> ORGANISM: Homo sapiens

<400> SEQUENCE: 28
ctaaatttca gttgacttgt catcttgatt tctggagacc acaaggtaat gaaaaataat    60
tacaagagtc ttccatctgt tgcagtatta aaatggtgag taagacaccc tga          113
```

RESTORATION OF THE CFTR FUNCTION BY SPLICING MODULATION

SEQUENCE LISTING

The Sequence Listing submitted in text format (.txt) filed on Jan. 12, 2018, named "SequenceListing.txt", created on Jan. 5, 2018, 30.7 KB), is incorporated herein by reference.

FIELD OF THE INVENTION

The present invention relates to oligonucleotides capable of binding to a Cystic Fibrosis Trans-membrane conductance Regulator (CFTR) pre-mRNA, thereby modulating its splicing. In particular, the present invention provides oligonucleotides and compositions thereof useful in methods for suppressing exon 10 skipping, optionally in combination with additional CFTR splicing modulators or other Cystic Fibrosis therapeutics.

BACKGROUND OF THE INVENTION

Cystic fibrosis (CF) is a common, severe autosomal recessive disease caused by mutations in the CFTR gene. The CFTR gene encodes for a chloride channel responsible for chloride transport in epithelial cells. The major manifestations of CF are in the lungs, with more than 90% mortality related to the respiratory disease. The disease in the respiratory tract is linked to the insufficient CFTR function in the airway epithelium.

As of today, approximately 2000 different mutations disrupting the CFTR functions have been identified worldwide, grouped into five distinct classes based on their effect on the CFTR function (Rogan M. P. et al., 2011). Class I includes mutations that lead to non-functional CFTR (large deletions and stop codon mutations). Class II mutations (including the common F508del) lead to aberrantly folded CFTR protein that is recognized by the cell quality control mechanism and subsequently degraded, resulting in the absence of mature CFTR protein at the apical cell membrane. Class III mutations lead to full-length CFTR protein being incorporated into the cell membrane, but with defective regulation so that no CFTR function is present. These three classes usually lead to a classic CF phenotype with pancreatic insufficiency, although the severity of lung disease is highly variable. CFTR mutations leading to defective chloride conductance are grouped into Class IV. Class V mutations involve transcription dysregulation, resulting in a decreased amount of otherwise normal CFTR. The latter two classes are often associated with a milder phenotype and pancreatic sufficiency. Specifically, CFTR that results from a class IV mutation inserts into the plasma membrane but exhibits reduced single-channel chloride ion conductance because of reduced chloride permeation and open channel probability. R117H, among the most common class IV mutations, occurs at a worldwide frequency approaching 0.5%. The R117H missense mutation causes an arginine-to-histidine substitution at residue 117. R117H-CFTR R domain is normally phosphorylated, and the nucleotide binding domain (NBD) binds adenosine triphosphate (ATP), but channel open time and thus chloride transport are reduced. Additionally, the degree of R117H-CFTR function depends on the length of the polythymidine tract in intron 9 on the same chromosome (which influences splicing efficiency) such that the longer thymidine tracts (9T>7T>5T) produce more functional R117H-CFTR. Clinical disease typically requires the R117H mutation in cis with 5T (Rogan M. P. et al., 2011; Kiesewetter et al., 1993). Found in <1% of patients with CF, class V mutations produce normal plasma membrane CFTR. The quantity, however, is generally reduced as a result of transcriptional dysregulation. Class V mutations frequently influence the splicing machinery and generate both aberrantly and correctly spliced mRNA, the levels of which vary among different patients and even among different organs of the same patients. Ultimately, the splice variants result in a reduced number of functioning CFTR in the plasma membrane (Rogan M. P. et al., 2011).

About 10-15% of CFTR mutations affect the correct splicing of the gene transcripts. Among these are two mutations that are included in the invention: the first is the splicing mutation 3849+10kb C-to-T which leads to inclusion of an 84 base pair cryptic exon in the mature messenger RNA (mRNA) (denoted "intron 22 cryptic exon inclusion" mutation). The mutation is the 12th most common CFTR mutation in the world, which occurs in hundreds of CF patients worldwide (Kerem et al., 1997; www.genet.sickkids.on.ca/; www.genet.sickkids.on.ca/resource/Table1.html). Correction of said aberrant splicing of the CFTR gene by "anti-sense" oligonucleotides was recently attempted by Friedman et al, 1999.

The second mutation is better described as a sequence variation in the poly $(TG)_n(T)_n$ tract at the acceptor splice site of exon 10 affecting the retention of this exon in the mature mRNA (denoted "exon 10 exclusion" mutation). Importantly, the skipping of the exon results in a non-functional gene transcript, as the exon encodes for the first 21% of the intra-cytoplasmic nucleotide binding fold 1 (NBF1), a critical region for the CFTR function (Cutting et al., 1990; Kerem B. S. et al., 1990). The CFTR gene in many individuals, healthy or CF patients, has an inherent splicing inefficiency of exon 10 due to the non-optimal length of the sequence $(TG)_n(T)_n$ with alleles carrying the $(TG)_{13}(T)_5$ combination generating the highest skipping levels (Chu et al., 2003; Hefferon et al., 2004; Groman et al., 2004).

One of the most promising therapeutic approaches for the treatment of genetic disorders caused by splicing mutations is based on splice-switching "anti-sense" oligonucleotides (AOs) administration. AOs are short synthetic RNA-like molecules chemically modified, which can anneal to motifs predicted to be involved in the pre-mRNA splicing. Their binding to selected sites is expected to mask the targeted region and promote normal splicing. AOs are highly specific for their targets and do not affect any other sequences in the cells. Several types of chemically modified AO molecules are commonly used including: 2'-O-methyl-phosphorothioate (2OMP), phosphorodiamidate morpholino oligomer (PMO), peptide nucleic acids (PNAs), 2-methoxyethyl phosphorothioate (MOE) and alternating locked nucleic acids (LNAs). Two of these are in more common use, 2OMP and PMO.

The AOs modifications maintain their stabilization, improve their target affinity, and provide favorable pharmacokinetic properties and biological stability. It has been conclusively shown that splice-switching AOs can redirect dystrophin pre-mRNA processing in murine models for Duchene Muscular Dystrophy (DMD) so that an exon carrying a premature protein termination signal (nonsense mutation) can be excluded from the mature gene transcript resulting in a shorter but still functional dystrophin isoform (Mann et al., 2001). Progress in dystrophin exon skipping has been rapid, with proof-of-concept studies reported in 2007 (van Deutekom et al., 2007) and 2009 (Kinali et al., 2009), and more recently with the publication of results from systemic administration to patients (Goemans et al., 2011; Cirak et al., 2011; Mendell J. R. et al., 2013). Systemic administration of OMP (5 weekly subcutaneous injections in 12 patients) showed dose-dependent molecular efficacy in patients with DMD (new dystrophin expression in muscle fibers), with a modest improvement in the 6-minute walk test (6 MWT) in 8/10 patients which entered a 12 week extension study (Goemans et al., 2011). Systemic administration of PMO (AVI-4658) (12 weekly IV infusions) (Cirak et al., 2001) caused in 7/19 of the patients exon skipping and dystrophin restoration. Moreover, in a recent study published by Mendell J R et al. (Mendell J. R. et al., 2013) the ability of AVI-4658 to induce dystrophin production and to improve distance walk on the 6 MWT was evaluated following 48 weeks of weekly IV infusions AVI-4658 restored functional dystrophin expression, causing a mean increase of 47% of dystrophin-positive fibers (change from baseline) together with an improvement in the 6 MWT.

In addition to induced exon skipping, AOs can be designed to mask splice-silencing elements that reduce exon recognition and subsequent inclusion in the mature mRNA. Spinal Muscular Atrophy (SMA) is a common autosomal recessive condition (Lorson, Rindt, & Shababi, 2010) caused by the loss of the SMN1 gene together with a C>T variation in SMN2 exon 7, leading to abnormal splicing in which SMN2 exon 7 is skipped, resulting in a non-functional gene product. AOs have been designed to mask nearby flanking SMN2 splice silencer elements to promote synthesis of full-length transcripts (Singh, Shishimorova, Cao, Gangwani, & Singh, 2009; Mitrpant et al., 2009). An intrathecally administration of morpholino oligomer to neonatal mouse pups with severe SMA was highly successful, significantly extending their survival (Porensky et al., 2012).

Different routes of AOs delivery have been examined in animal models and applied in clinical trials, chosen primarily according to the target tissue. For example, 2OMP was administrated to DMD patients (PRO-051) by local intramuscular injection (van Deutekom et al., 2007), and by abdominal subcutaneous injections (Goemans et al., 2011). 2OMP was also administrated to a SMA mouse model by intracerebroventricular injection (Williams et al., 2009; Hua et al., 2010). PMO was administrated to a DMD mouse model by intramuscular injection (Gebski, Mann, Fletcher, & Wilton, 2003), and repeated weakly intraperitoneal injections (Goyenvalle et al., 2010). PMO was also administrated to a SMA mouse model by intracerebroventricular injection (Porensky et al., 2012), and to DMD patients (AVI-4658) by local intramuscular injection (Kinali et al., 2009), or intravenously administration (Cirak et al., 2011; Mendell et al., 2013).

There remains a constant need in the field of Cystic Fibrosis management for novel, potent therapeutics, designed to overcome the numerous mutations in the CFTR gene identified thus far, and restore CFTR function.

SUMMARY OF THE INVENTION

The present invention provides compositions comprising oligonucleotides capable of binding to a CFTR pre-mRNA, thereby modulating splicing and restoring or enhancing the function of the CFTR gene product. The present invention thus identifies sequences within the CFTR pre-mRNA which are targeted in order to modulate the splicing cascade of the CFTR pre-mRNA. Modulating CFTR pre-mRNA splicing, as demonstrated in the present invention, can avoid improper skipping of canonical exons and can also avoid improper recognition of intron sequences as exons. As a result of the modulation of splicing, a functional CFTR protein is produced by an otherwise aberrant CFTR allele.

The present invention stems in part from the finding that artificial "anti-sense" polynucleotide molecules are able to target and bind predetermined sequences at the pre-mRNA molecule of the CFTR gene, and that said binding can modulate the splicing of said pre-mRNA molecule into a mature mRNA which is subsequently translated into a functional CFTR protein. The targets within a CFTR pre-mRNA molecule are those discovered to be involved in splicing, either indirectly, by affecting the splicing of adjacent as well as more remote sequences, or directly, by affecting their own splicing.

Thus, in one aspect, the present invention provides a synthetic polynucleotide molecule, comprising a nucleotide sequence comprising a sequence of at least 18 consecutive nucleotide bases, wherein said synthetic polynucleotide molecule is capable of binding to a pre-mRNA transcript of the CFTR gene, and suppressing exon 10 exclusion from the mature CFTR mRNA.

In certain embodiments, the nucleotide sequence comprises at least 18 nucleotides e.g. at least 18 or at least 21 nucleotides. In other certain embodiments, the nucleotide sequence comprises about 20 to 30 nucleotides e.g. about 20 to 28, about 20 to 26 or about 22 to 26 nucleotides. In specific embodiments, the nucleotide sequence comprises 22, 23, 24, 25, or 26 nucleotides. Each possibility represents a separate embodiment of the present invention.

In order to suppress exon 10 exclusion, the synthetic polynucleotide must bind to an exon 10 splicing-silencing-motif found within and/or adjacent to exon 10 of the CFTR gene. Thus, in certain embodiments, the nucleotide sequence is complementary to the nucleotide sequence set forth in SEQ ID NO: 2, or to a fragment thereof. Each possibility represents a separate embodiment of the present invention.

In certain embodiments, said nucleotide sequence comprises a nucleotide sequence set forth in SEQ ID NO: 10 or an active fragment of said nucleotide sequence. Each possibility represents a separate embodiment of the present invention.

The interaction between the synthetic polynucleotide molecules of the present invention and their targets, CFTR pre-mRNA molecules, is primarily a base-base interaction, wherein the nucleotides of the synthetic polynucleotide molecules of the present invention have a base sequence complementary to the base sequence of their CFTR pre-mRNA target(s). It therefore should be understood that the type of backbone used to link the nucleotides of the synthetic polynucleotide molecule of the present invention is secondary, as long as it is known by a man of the art to be appropriate for carrying bases and targeting single stranded DNA and/or RNA molecules. Many such backbones are long known in the art, including the following non-limiting examples of a phosphate-ribose backbone (as in RNA), a phosphate-deoxyribose backbone (as in DNA), a phosphorothioate backbone, a 2'-O-methyl-phosphorothioate (2OMP) backbone, a phosphorodiamidate morpholino (PMO) backbone, a peptide nucleic acid (PNA) backbone, a 2-methoxyethyl phosphorothioate (MOE) backbone, and an alternating locked nucleic acids (LNAs) backbone (reviewed in Lu et al., 2011), all of which are considered appropriate backbones according to the present invention, and each possibility represents a separate embodiment of the present invention.

Thus, in certain embodiments, the synthetic polynucleotide molecule of the present invention comprises a sequence of at least about 18 consecutive nucleotide bases, wherein each nucleotide comprises a base which is independently selected from adenine, guanine, cytosine, uracil and optionally thymine, attached to each other via one of said backbones.

In another aspect, the present invention provides a pharmaceutical composition comprising a synthetic polynucleotide molecule as described above, and a pharmaceutically acceptable carrier.

In certain embodiments, the pharmaceutical composition is formulated for oral, nasal, aerosol, inhalational, abdominal, subcutaneous, intra-peritoneal or intravenous administration. Each possibility represents a separate embodiment of the present invention.

Being a long-known and well-studied disease, certain drugs and agents are already known in the art for the treatment of Cystic Fibrosis patients. Thus, in certain embodiments, the pharmaceutical composition of the present invention further comprises at least one additional anti-Cystic-Fibrosis agent.

In certain such embodiments, the additional anti-Cystic-Fibrosis agent is selected from the group consisting of a CFTR-splicing-modulating agent, a CFTR potentiator and a CFTR corrector. Each possibility represents a separate embodiment of the present invention.

In a more specific such embodiment, said CFTR-splicing-modulating agent is a synthetic polynucleotide molecule capable of suppressing intron 22 cryptic exon inclusion in the mature CFTR mRNA. In a more specific such embodiment, said CFTR potentiator is N-(2,4-Di-tert-butyl-5-hydroxyphenyl)-4-oxo-1,4-dihydroquinoline-3-carboxamide (Ivacaftor). In a more specific such embodiment, said CFTR corrector is selected from the group consisting of 3-[5-(2-fluorophenyl)-1,2,4-oxadiazol-3-yl]benzoic acid (Ataluren) and 3-{6-{[1-(2,2-difluoro-1,3-benzodioxol-5-yl)cyclopropanecarbonyl]amino}-3-methylpyridin-2-yl}benzoic acid (Lumacaftor). Each possibility represents a separate embodiment of the present invention.

According to other embodiments, the pharmaceutical composition comprises the synthetic polynucleotide molecule described above capable of suppressing exon 10 exclusion from the mature CFTR mRNA, and a synthetic polynucleotide molecule capable of suppressing intron 22 cryptic exon inclusion in the mature CFTR mRNA.

In an embodiment, the pharmaceutical composition comprises a synthetic polynucleotide molecule comprising the nucleotide sequence set forth in SEQ ID NO: 10 or an active fragment of said nucleotide sequence, and a synthetic polynucleotide molecule comprising the nucleotide sequence set forth in SEQ ID NO: 6, SEQ ID NO: 7, SEQ ID NO: 8 or SEQ ID NO: 9. Each possibility represents a separate embodiment of the present invention.

In another aspect, the present invention provides a synthetic polynucleotide molecule as described above, for use in the modulation of splicing of a CFTR pre-mRNA. Any change in ratio between certain CFTR splicing variants is also considered the result of splicing modulation. Each possibility represents a separate embodiment of the present invention.

Thus, according to certain embodiments, the synthetic polynucleotide molecule described above is for use in reducing the level of an mRNA molecule comprising the nucleotide sequence set forth in SEQ ID NO: 12. In other embodiments, the synthetic polynucleotide molecule described above is for use in increasing the level of an mRNA molecule comprising the nucleotide sequence set forth in SEQ ID NO: 1. In certain embodiments, the synthetic polynucleotide described above comprises the nucleotide sequence set forth in SEQ ID NO: 10, or an active fragment of said nucleotide sequence.

Being a genetic disease, Cystic Fibrosis currently cannot be cured, but its clinical manifestations can be treated by the oligonucleotides of the present invention, for a marked increase and/or improvement in a patient's clinical status and quality of life. Thus, in a further aspect, the present invention provides a method for improving at least one clinical parameter of Cystic Fibrosis in a patient in need thereof, comprising the step of administering a therapeutically effective amount of a synthetic polynucleotide molecule as described above to said patient.

In certain embodiments, the clinical parameter is selected from the group consisting of lung function, time to the first pulmonary exacerbation, a change in weight, a change in height, a change in Body Mass Index (BMI), a change in the concentration of sweat chloride, number and/or duration of pulmonary exacerbations, total number of days of hospitalization for pulmonary exacerbations, or the need for antibiotic therapy for sinopulmonary signs or symptoms. Each possibility represents a separate embodiment of the present invention.

In certain embodiments, the method further comprises administering at least one additional anti-Cystic-Fibrosis agent to said patient.

In certain such embodiments, said additional anti-Cystic-Fibrosis agent is selected from the group consisting of a CFTR-splicing-modulating agent, a CFTR potentiator and a CFTR corrector. Each possibility represents a separate embodiment of the present invention. More specific embodiments of said agents are described above.

In certain embodiments, the method comprises administering the synthetic polynucleotide molecule as described above capable of suppressing exon 10 exclusion from the mature CFTR mRNA, and further administering a synthetic polynucleotide molecule capable of suppressing intron 22 cryptic exon inclusion in the mature CFTR mRNA.

In certain such embodiments, the method comprises administering a synthetic polynucleotide molecule comprising the nucleotide sequence set forth in SEQ ID NO: 10 or an active fragment of said nucleotide sequence, and further administering a synthetic polynucleotide molecule comprising the nucleotide sequence set forth in SEQ ID NO: 6, SEQ ID NO: 7, SEQ ID NO: 8, or SEQ ID NO: 9. Each possibility represents a separate embodiment of the present invention.

In certain embodiments, the administration of said synthetic polynucleotide molecule of the present invention and the administration of said at least one additional anti-Cystic-Fibrosis agent are independently oral, nasal, aerosol, inhalational, abdominal, subcutaneous, intra-peritoneal or intravenous administration. Each possibility represents a separate embodiment of the present invention. It should be understood that the selection of an administration route depends on the nature of the therapeutic agent and on the site of its intended effect, and thus certain agents may be administrated via the same or different administration routes.

In a further aspect, the present invention provides a kit comprising a synthetic polynucleotide molecule as described above, and an additional anti-Cystic-Fibrosis agent. In certain embodiments said additional anti-Cystic-Fibrosis agent is selected from the group consisting of a CFTR-splicing-modulating agent, a CFTR potentiator and a CFTR corrector. Each possibility represents a separate embodiment of the present invention. More specific embodiments of said agents are described above.

In other certain embodiments, said kit comprises a synthetic polynucleotide molecule as described above capable of suppressing exon 10 exclusion from the mature CFTR mRNA and a synthetic polynucleotide molecule capable of suppressing intron 22 cryptic exon inclusion in the mature CFTR mRNA.

In specific such embodiments, said kit comprises a synthetic polynucleotide molecule comprising the nucleotide sequence set forth in SEQ ID NO: 10 or an active fragment of said nucleotide sequence, and a synthetic polynucleotide molecule comprising the nucleotide sequence set forth in SEQ ID NO: 6, SEQ ID NO: 7, SEQ ID NO: 8, or SEQ ID NO: 9. Each possibility represents a separate embodiment of the present invention.

In certain embodiments, said synthetic polynucleotide and said additional anti-Cystic-Fibrosis agent are comprised in one or more, the same or different pharmaceutical compositions. In other certain embodiments, said one or more pharmaceutical compositions are each independently formulated for oral, nasal, acrosol, inhalation, abdominal, subcutaneous, intra-peritoneal or intravenous administration. Each possibility represents a separate embodiment of the present invention.

In a further aspect, the present invention provides a synthetic polynucleotide molecule, comprising a nucleotide sequence comprising a sequence of at least 20 consecutive nucleotide bases, wherein said synthetic polynucleotide molecule is capable of binding to a pre-mRNA transcript of the CFTR gene, and suppressing intron 22 cryptic exon inclusion in the mature CFTR mRNA. The phrase "suppress intron 22 cryptic exon inclusion" as used herein refers to lowering the occurrence of the addition of 84 nucleotides (SEQ ID NO: 5) found within intron 22 of the CFTR gene to the mature CFTR mRNA, leading to degradation of said mRNA by the nonsense mediated mRNA decay (NMD) mechanism, as illustrated in FIG. 6. In certain embodiments, said nucleotide sequence is complementary to the nucleotide sequence set forth in SEQ ID NO: 3, or to a fragment thereof. In other certain embodiments, said nucleotide sequence comprises a nucleotide sequence set forth in SEQ ID NO: 6, SEQ ID NO: 7, SEQ ID NO: 8 or SEQ ID NO: 9. Each possibility represents a separate embodiment of the present invention.

The present invention further provides, in a related aspect, a pharmaceutical composition comprising a synthetic polynucleotide molecule as described above, and a pharmaceutically acceptable carrier.

In a further related aspect, the present invention provides a synthetic polynucleotide molecule as described above, for use in the modulation of splicing of a CFTR pre-mRNA. In certain embodiments, said synthetic polynucleotide molecule is for use in reducing the level of an mRNA molecule comprising the nucleotide sequence set forth in SEQ ID NO: 11. In other certain embodiments, said synthetic polynucleotide molecule is for use in increasing the level of an mRNA molecule comprising the nucleotide sequence set forth in SEQ ID NO: 1. In other certain embodiments, said synthetic polynucleotide molecule comprises the nucleotide sequence set forth in SEQ ID NO: 6, SEQ ID NO: 7, SEQ ID NO: 8 or SEQ ID NO: 9. Each possibility represents a separate embodiment of the present invention.

The invention further provides, in an aspect, a method for improving at least one clinical parameter of Cystic Fibrosis in a patient in need thereof, comprising the step of administering a therapeutically effective amount of a synthetic polynucleotide molecule as described above to said patient. In certain embodiments, said clinical parameter is selected from the group consisting of lung function, time to the first pulmonary exacerbation, change in weight, change in height, a change in Body Mass Index (BMI), change in the concentration of sweat chloride, number and/or duration of pulmonary exacerbations, total number of days of hospitalization for pulmonary exacerbations, and the need for antibiotic therapy for sinopulmonary signs or symptoms. Each possibility represents a separate embodiment of the present invention.

BRIEF DESCRIPTION OF THE DRAWINGS

FIG. 2: illustrates the binding site (underlined) of oligonucleotide 5 used to suppress aberrant splicing of exon 10 of the CFTR gene. Small case sequences intron 9 and intron 10, respectively. Upper case sequence—exon 10.

DETAILED DESCRIPTION OF THE INVENTION

The present invention provides oligonucleotides and compositions comprising said oligonucleotides, capable of binding to a CFTR pre-mRNA, thereby modulating splicing and restoring or enhancing the function of the CFTR gene product. The present invention thus identifies sequences within the CFTR pre-mRNA which are targeted in order to modulate the splicing cascade of the CFTR pre-mRNA. Modulating CFTR pre-mRNA splicing, as demonstrated in the present invention, can avoid improper skipping of canonical exons and can also avoid improper recognition of intron sequences as exons. As a result of the modulation of splicing, a functional CFTR protein is produced by an otherwise aberrant CFTR allele.

The present invention stems in part from the finding that artificial "anti-sense" polynucleotide molecules are able to target and bind predetermined sequences at the pre-mRNA molecule of the CFTR gene, and that said binding modulates the splicing of said pre-mRNA molecule into mature mRNA, which subsequently translates into a functional CFTR protein. The targets within a CFTR pre-mRNA molecule are those discovered to be involved in splicing, either indirectly, by affecting the splicing of adjacent as well as remote sequences, or directly, by affecting their own splicing.

Thus, in one aspect, the present invention provides a synthetic polynucleotide molecule, comprising a nucleotide sequence comprising a sequence of at least 18 consecutive nucleotide bases, wherein said synthetic polynucleotide molecule is capable of binding to a pre-mRNA transcript of the CFTR gene, and suppressing exon 10 exclusion from the mature CFTR mRNA.

The phrase "a nucleotide sequence comprising a sequence of at least 18 consecutive nucleotide bases" as used herein refers to a sequence of at least 18 consecutive nucleotides linked by a backbone, wherein each nucleotide comprises a base. In certain embodiments, said base is selected from the group consisting of adenine, guanine, cytosine, uracil and optionally thymine. In other certain embodiments, said base is selected from the group consisting of adenine, guanine, cytosine and uracil. Each possibility represents a separate embodiment of the present invention.

Figure 1:
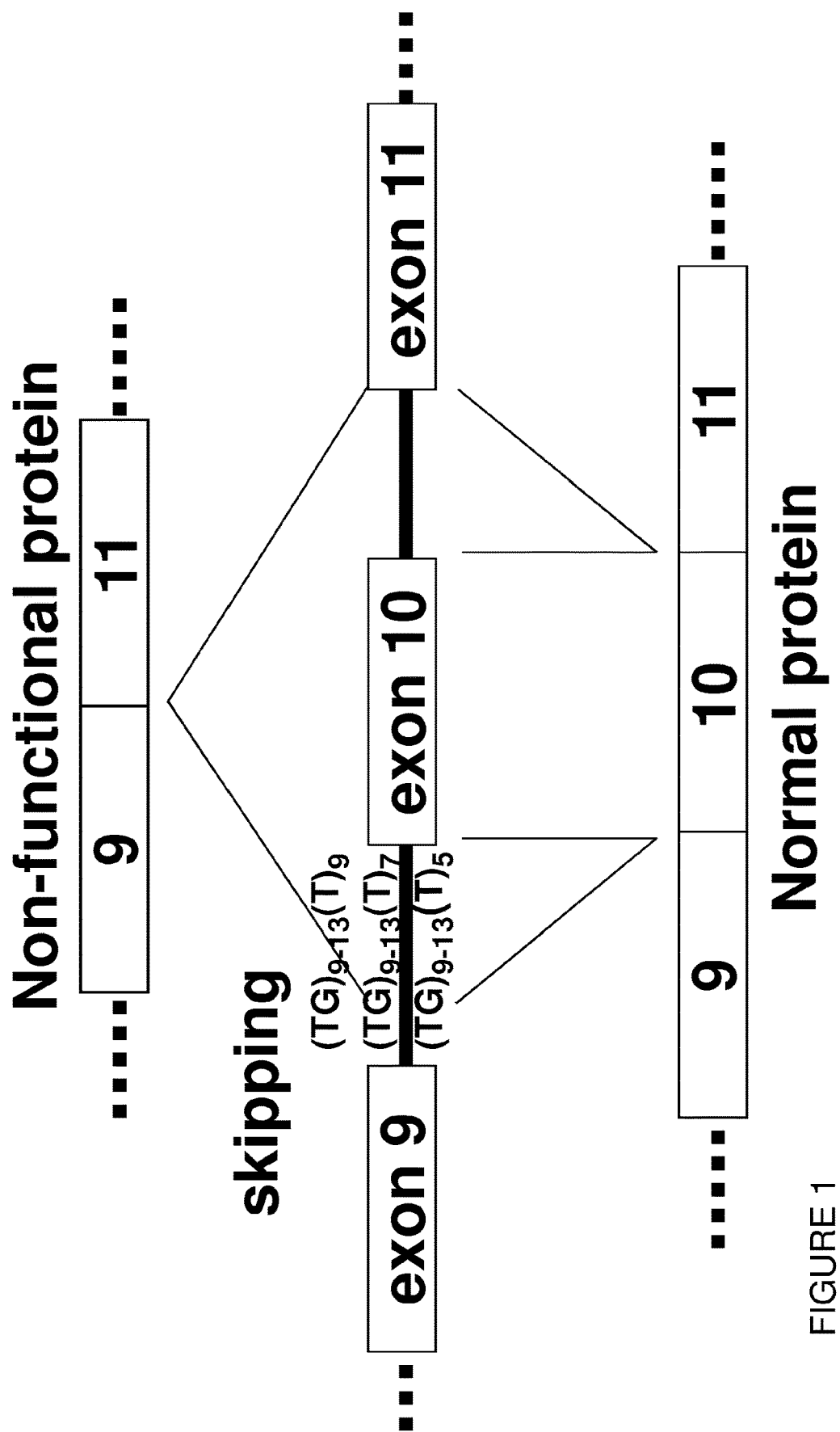
FIG. 1: illustrates the effect of aberrant splicing of exon 10 of the CFTR gene. Bottom—upon normal splicing, exons 9 becomes adjacent to exon 10, and exon 10 becomes adjacent to exon 11. Middle—the poly $(TG)_n(T)_n$ tract at the acceptor splice site of exon 10 affects the retention of this exon in the mature mRNA, $(TG)_{13}(T)_5$ generating the highest skipping levels. Top—the skipping of the exon results in a non-functional gene transcript.

The phrase "suppressing exon 10 exclusion" as used herein refers to lowering the occurrence of the exclusion of exon 10 from the mature CFTR mRNA (as in SEQ ID NO: 12), also known as "exon 10 skipping", which upon translation results in a non-functional protein, as illustrated in FIG. 1.

In certain embodiments, the nucleotide sequence comprises at least 18 nucleotides e.g. at least 18, at least 19, at least 20 or at least 21 nucleotides. In other certain embodiments, the nucleotide sequence comprises about 20 to 30 nucleotides e.g. about 20 to 28, about 20 to 26 or about 22 to 26 nucleotides. In specific embodiments, the nucleotide sequence comprises 22, 23, 24, 25, or 26 nucleotides. Each possibility represents a separate embodiment of the present invention.

In order to suppress exon 10 exclusion, the synthetic polynucleotide must bind to an exon 10 splicing-silencing-motif found within and/or adjacent to exon 10 of the CFTR gene. Thus, in certain embodiments, the nucleotide sequence is complementary to the nucleotide sequence set forth in SEQ ID NO: 2, or to a fragment thereof. Each possibility represents a separate embodiment of the present invention.

The term "exon 10 splicing-silencing-motif" as used herein refers to negatively acting elements involved in exon recognition, i.e any nucleotide sequences within the CFTR pre-mRNA, the binding of which by an exogenous agent, e.g. the oligonucleotides of the present invention, decreases the incidence of exon 10 skipping, increases the incidence of exon 10 inclusion, and/or increasing the level of full length normal CFTR mRNA (as assessed by conventional methods, e.g. by RT-PCR across the CFTR mRNA transcripts).

The phrase "or to a fragment thereof" as used herein refers to any consecutive fragment of the nucleotide sequence in SEQ ID NO: 2 or SEQ ID NO: 3, which is at least equal in length to the nucleotide sequence comprised in the synthetic polynucleotide. For example, if the synthetic polynucleotide molecule of the present invention comprises a sequence of 18 consecutive nucleotides, the fragment of the nucleotide sequence in SEQ ID NO: 2 or SEQ ID NO: 3 to which it binds is also 18 nucleotides in length.

In certain embodiments, said nucleotide sequence comprises a nucleotide sequence set forth in SEQ ID NO: 10 or an active fragment of said nucleotide sequence. Each possibility represents a separate embodiment of the present invention.

The phrase "active fragment of a nucleotide sequence" as used herein refers to a fragment that is 100% identical to a contiguous portion of the full nucleotide sequence, providing that at least about 30%, 40%, 50%, 60%, 70%, 80% or 90% of the activity of the original nucleotide sequence is retained. Each possibility represents a separate embodiment of the present invention.

According to some embodiments, said active fragment consists at least about 30%, 40%, 50%, 60%, 70%, 80% or 90% of the original nucleotide sequence. Each possibility represents a separate embodiment of the present invention.

The interaction between the synthetic polynucleotide molecule of the present invention and their target, a CFTR pre-mRNA, is primarily a base-base interaction, wherein the nucleotides of the synthetic polynucleotide molecule of the present invention have a base sequence complementary to the base sequence of their target CFTR pre-mRNA. It therefore should be understood that the type of backbone used to link the nucleotides of the synthetic polynucleotide molecule of the present invention is secondary, as long as it is known to a man of average skill in the art to be appropriate for carrying bases for targeting single stranded DNA and/or RNA molecules. Many such backbones are long known in the art, including the following non-limiting examples of a phosphate-ribose backbone (as in RNA), a phosphate-deoxyribose backbone (as in DNA), a phosphorothioate backbone, a 2'-O-methyl-phosphorothioate (2OMP) backbone, a phosphorodiamidate morpholino (PMO) backbone, a peptide nucleic acid (PNA) backbone, a 2-methoxyethyl phosphorothioate (MOE) backbone, and an alternating locked nucleic acids (LNAs) backbone, all of which are considered appropriate backbones according to the present invention, and each possibility represents a separate embodiment of the present invention.

In certain embodiments, said backbone is selected from the group consisting of a phosphorothioate backbone, a 2'-O-methyl-phosphorothioate (2OMP) backbone, a phosphorodiamidate morpholino (PMO) backbone, a peptide nucleic acid (PNA) backbone, a 2-methoxyethyl phosphorothioate (MOE) backbone, and an alternating locked nucleic acids (LNAs) backbone. In more specific embodiments, said backbone is selected from the group consisting of a phosphorothioate backbone, a 2'-O-methyl-phosphorothioate (2OMP) backbone, a phosphorodiamidate morpholino (PMO) backbone and a 2-methoxyethyl phosphorothioate (MOE) backbone. Each possibility represents a separate embodiment of the present invention.

In another aspect, the present invention provides a pharmaceutical composition comprising a synthetic polynucleotide molecule as described above, and a pharmaceutically acceptable carrier.

The term "pharmaceutically acceptable carrier" as used herein refers to any of the standard pharmaceutical carriers known in the field such as sterile solutions, tablets, coated tablets, and capsules. Typically such carriers contain excipients such as starch, milk, sugar, certain types of clay, gelatin, stearic acids or salts thereof, magnesium or calcium stearate, talc, vegetable fats or oils, gums, glycols, or other known excipients. Such carriers may also include flavor and color additives or other ingredients. Examples of pharmaceutically acceptable carriers include, but are not limited to, the following: water, saline, buffers, inert, nontoxic solids (e.g., mannitol, talc). Compositions comprising such carriers are formulated by well-known conventional methods. Depending on the intended mode of administration and the intended use, the compositions may be in the form of solid, semi-solid, or liquid dosage forms, such, for example, as powders, granules, crystals, liquids, suspensions, liposomes, nanoparticles, nano-emulsions, pastes, creams, salves, etc., and may be in unit-dosage forms suitable for administration of relatively precise dosages.

In certain embodiments, the pharmaceutical composition is formulated for oral, nasal, aerosol, inhalational, abdominal, subcutaneous, intra-peritoneal or intravenous administration. Each possibility represents a separate embodiment of the present invention.

Figure 5:
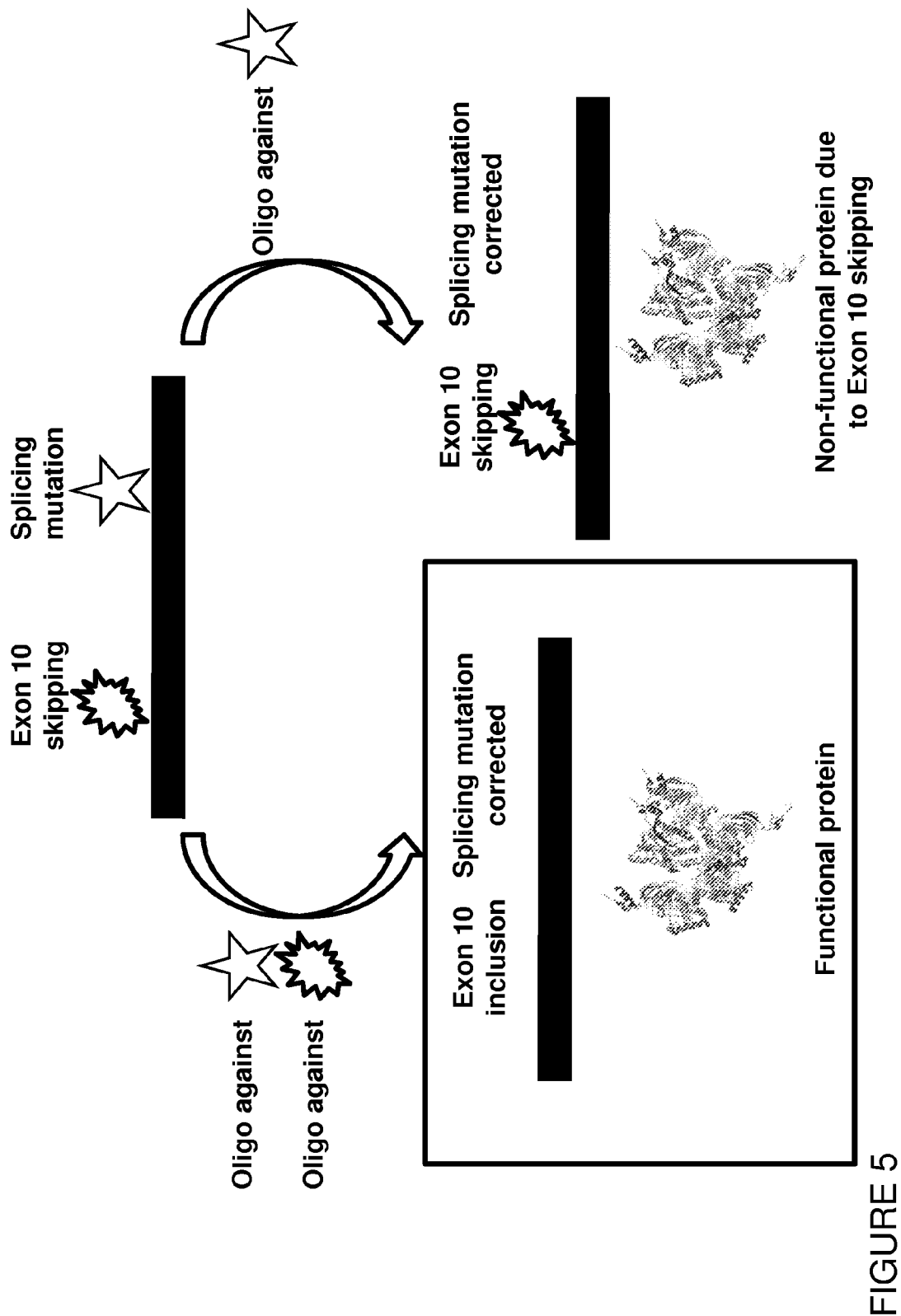
FIG. 5: illustrates the advantage of combining oligonucleotides targeted to correct CFTR exon 10 skipping with other CFTR therapies, e.g. oligonucleotides targeted to correct CFTR splicing mutation.

Being a long-known and well-studied disease, certain drugs and agents are known in the art for the treatment of Cystic Fibrosis patients. Administrating a synthetic polynucleotide molecule according to the present invention with one or more of these drugs may be crucial in achieving beneficial therapeutic results (see e.g. FIG. 5). Thus, in certain embodiments, the pharmaceutical composition of the present invention further comprises at least one additional anti-Cystic-Fibrosis agent.

In certain such embodiments, said additional anti-Cystic-Fibrosis agent is selected from the group consisting of a CFTR-splicing-modulating agent, a CFTR potentiator and a CFTR corrector. Each possibility represents a separate embodiment of the present invention.

In a more specific such embodiment, said CFTR-splicing-modulating agent is a synthetic polynucleotide molecule capable of suppressing intron 22 cryptic exon inclusion in the mature CFTR mRNA. In another more specific such embodiment, said CFTR potentiator is N-(2,4-Di-tert-butyl-5-hydroxyphenyl)-4-oxo-1,4-dihydroquinoline-3-carboxamide (Ivacaftor). In another more specific such embodiment, said CFTR corrector is selected from the group consisting of 3-[5-(2-fluorophenyl)-1,2,4-oxadiazol-3-yl] benzoic acid (Ataluren) and 3-{6-{[1-(2,2-difluoro-1,3-benzodioxol-5-yl)cyclopropanecarbonyl]amino}-3-methylpyridin-2-yl}benzoic acid (Lumacaftor). Each possibility represents a separate embodiment of the present invention.

According to other embodiments, the pharmaceutical composition comprises the synthetic polynucleotide molecule described above, capable of suppressing exon 10 exclusion from the mature CFTR mRNA, and a synthetic polynucleotide molecule, capable of suppressing intron 22 cryptic exon inclusion in the mature CFTR mRNA.

In an embodiment, the pharmaceutical composition comprises the synthetic polynucleotide molecule described above, capable of suppressing exon 10 exclusion from the mature CFTR mRNA, and a synthetic polynucleotide molecule comprising the nucleotide sequence set forth in SEQ ID NO: 6, SEQ ID NO: 7, SEQ ID NO: 8 or SEQ ID NO: 9. Each possibility represents a separate embodiment of the present invention.

In an embodiment, the pharmaceutical composition comprises a synthetic polynucleotide molecule comprising the nucleotide sequence set forth in SEQ ID NO: 10 or an active fragment of said nucleotide sequence, and a synthetic polynucleotide molecule, capable of suppressing intron 22 cryptic exon inclusion in the mature CFTR mRNA. Each possibility represents a separate embodiment of the present invention.

In an embodiment, the pharmaceutical composition comprises a synthetic polynucleotide molecule comprising the nucleotide sequence set forth in SEQ ID NO: 10 or an active fragment of said nucleotide sequence, and a synthetic polynucleotide molecule comprising the nucleotide sequence set forth in SEQ ID NO: 6, SEQ ID NO: 7, SEQ ID NO: 8 or SEQ ID NO: 9. Each possibility represents a separate embodiment of the present invention.

In another aspect, the present invention provides a synthetic polynucleotide molecule as described above, for use in the modulation of splicing of a CFTR pre-mRNA. The phrase "modulation of splicing" as used herein refers to affecting a change in the level of any RNA or mRNA variant produced by the CFTR native pre-mRNA, e.g. causing an increase or decrease in the level of abnormal CFTR mRNA not comprising exon 10, causing an increase or decrease in the level of normal, full CFTR mRNA, and/or causing an increase or decrease in the level of abnormal CFTR RNA or mRNA comprising a premature termination codon (nonsense codon). It is therefore evident that any change in ratio between certain CFTR splicing variants is also considered to be the result of splicing modulation. Each possibility represents a separate embodiment of the present invention.

Thus, according to certain embodiments, the synthetic polynucleotide molecule described above is for use in the modulation of splicing of a CFTR pre-mRNA carrying a mutation of CFTR mutation classes I to V, especially of classes IV and V. Each possibility represents a separate embodiment of the present invention. In certain such embodiments, the synthetic polynucleotide molecule described above is for use in correcting or improving chloride transport through the CFTR channel, or in increasing the production of functional CFTR protein. Each possibility represents a separate embodiment of the present invention. In other certain such embodiments, the synthetic polynucleotide molecule described above is for use in patients carrying CFTR mutations with residual CFTR function such as mutations of mutation classes I to V, preferably classes IV and/or V. Each possibility represents a separate embodiment of the present invention.

According to other certain embodiments, the synthetic polynucleotide molecule described above is for use in reducing the level of an mRNA molecule comprising the nucleotide sequence set forth in SEQ ID NO: 12.

In other embodiments, the synthetic polynucleotide molecule described above is for use in increasing the level of an mRNA molecule comprising the nucleotide sequence set forth in SEQ ID NO: 1.

In certain embodiments, the synthetic polynucleotide described above comprises the nucleotide sequence set forth in SEQ ID NO: 10, or an active fragment of said nucleotide sequence. Each possibility represents a separate embodiment of the present invention.

In a further aspect, the present invention provides a method for improving at least one clinical parameter of Cystic Fibrosis in a patient in need thereof, comprising the step of administering a therapeutically effective amount of a synthetic polynucleotide molecule as described above to said patient. Being a genetic disease, Cystic Fibrosis currently cannot be cured, but its clinical manifestations and/or symptoms can be treated by the oligonucleotides of the present invention, for a marked increase and/or improvement in a patient's clinical status and quality of life.

The term "improving" as used herein refers to a favorable change, i.e. an increase or a decrease of at least 5%, at least 10%, at least 15%, at least 20%, at least 25%, at least 30%, at least 35%, at least 40%, at least 45%, or at least 50% in a certain Cystic Fibrosis clinical parameter.

The term "a therapeutically effective amount" as used herein refers to an amount necessary for improving at least one clinical parameter of Cystic Fibrosis or reducing the severity of at least one clinical parameter of Cystic Fibrosis in a patient. The therapeutically effective amount differs according to the patient's status, the synthetic polynucleotide molecule's administration route, excipient usage and co-usage of other active agents.

Thus, in certain embodiments, the clinical parameter is selected from the group consisting of lung function, time to the first pulmonary exacerbation, a change in weight, a change in height, a change in Body Mass Index (BMI), a change in the concentration of sweat chloride, number and/or duration of pulmonary exacerbations, total number of days of hospitalization for pulmonary exacerbations, or the need for antibiotic therapy for sinopulmonary signs or symptoms. Each possibility represents a separate embodiment of the present invention.

In certain embodiments, the method further comprises administering at least one additional anti-Cystic-Fibrosis agent to said patient.

In certain such embodiments, said additional anti-Cystic-Fibrosis agent is selected from the group consisting of a CFTR-splicing-modulating agent, a CFTR potentiator and a CFTR corrector. Each possibility represents a separate embodiment of the present invention.

In a more specific such embodiment, said CFTR-splicing-modulating agent is a synthetic polynucleotide molecule capable of suppressing intron 22 cryptic exon inclusion in the mature CFTR mRNA. In another more specific such embodiment, said CFTR potentiator is N-(2,4-Di-tert-butyl-5-hydroxyphenyl)-4-oxo-1,4-dihydroquinoline-3-carboxamide (Ivacaftor). In another more specific such embodiment, said CFTR corrector is selected from the group consisting of 3-[5-(2-fluorophenyl)-1,2,4-oxadiazol-3-yl]benzoic acid (Ataluren) and 3-{6-{[1-(2,2-difluoro-1,3-benzodioxol-5-yl)cyclopropanecarbonyl]amino}-3-methylpyridin-2-yl}benzoic acid (Lumacaftor). Each possibility represents a separate embodiment of the present invention.

In certain embodiments, the method comprises administering the synthetic polynucleotide molecule as described above, capable of suppressing exon 10 exclusion from the mature CFTR mRNA, and further administering a synthetic polynucleotide molecule, capable of suppressing intron 22 cryptic exon inclusion in the mature CFTR mRNA.

In certain such embodiments, the method comprises administering the synthetic polynucleotide molecule as described above, capable of suppressing exon 10 exclusion from the mature CFTR mRNA, and further administering a synthetic polynucleotide molecule comprising the nucleotide sequence set forth in SEQ ID NO: 6, SEQ ID NO: 7, SEQ ID NO: 8, or SEQ ID NO: 9. Each possibility represents a separate embodiment of the present invention.

In certain such embodiments, the method comprises administering a synthetic polynucleotide molecule comprising the nucleotide sequence set forth in SEQ ID NO: 10 or an active fragment of said nucleotide sequence, and further administering a synthetic polynucleotide molecule, capable of suppressing intron 22 cryptic exon inclusion in the mature CFTR mRNA. Each possibility represents a separate embodiment of the present invention.

In certain such embodiments, the method comprises administering a synthetic polynucleotide molecule comprising the nucleotide sequence set forth in SEQ ID NO: 10 or an active fragment of said nucleotide sequence, and further administering a synthetic polynucleotide molecule comprising the nucleotide sequence set forth in SEQ ID NO: 6, SEQ ID NO: 7, SEQ ID NO: 8, or SEQ ID NO: 9. Each possibility represents a separate embodiment of the present invention.

In certain embodiments, the administration of said therapeutically effective amount of a synthetic polynucleotide molecule of the present invention and the administration of said at least one additional anti-Cystic-Fibrosis agent are independently oral, nasal, aerosol, inhalational, abdominal, subcutaneous, intra-peritoneal or intravenous administration. Each possibility represents a separate embodiment of the present invention. It should be understood that the selection of an administration route depends on the nature of the therapeutic agent and the site of its intended effect, and thus certain agents may be administrated via the same or different administration routes.

In a further aspect, the present invention provides a kit comprising a synthetic polynucleotide molecule as described above, and an additional anti-Cystic-Fibrosis agent. In certain embodiments said additional anti-Cystic-Fibrosis agent is selected from the group consisting of a CFTR-splicing-modulating agent, a CFTR potentiator and a CFTR corrector. Each possibility represents a separate embodiment of the present invention.

In a more specific such embodiment, said CFTR-splicing-modulating agent is a synthetic polynucleotide molecule capable of suppressing intron 22 cryptic exon inclusion in the mature CFTR mRNA. In another more specific such embodiment, said CFTR potentiator is N-(2,4-Di-tert-butyl-5-hydroxyphenyl)-4-oxo-1,4-dihydroquinoline-3-carboxamide (Ivacaftor). In another more specific such embodiment, said CFTR corrector is selected from the group consisting of 3-[5-(2-fluorophenyl)-1,2,4-oxadiazol-3-yl]benzoic acid (Ataluren) and 3-{6-{[1-(2,2-difluoro-1,3-benzodioxol-5-yl)cyclopropanecarbonyl]amino}-3-methylpyridin-2-yl}benzoic acid (Lumacaftor). Each possibility represents a separate embodiment of the present invention.

In other certain embodiments, said kit comprises a synthetic polynucleotide molecule as described above, capable of suppressing exon 10 exclusion from the mature CFTR mRNA, and a synthetic polynucleotide molecule, capable of suppressing intron 22 cryptic exon inclusion in the mature CFTR mRNA.

In specific such embodiments, said kit comprises a synthetic polynucleotide molecule as described above, capable of suppressing exon 10 exclusion from the mature CFTR mRNA, and a synthetic polynucleotide molecule comprising the nucleotide sequence set forth in SEQ ID NO: 6, SEQ ID NO: 7, SEQ ID NO: 8, or SEQ ID NO: 9. Each possibility represents a separate embodiment of the present invention.

In specific such embodiments, said kit comprises a synthetic polynucleotide molecule comprising the nucleotide sequence set forth in SEQ ID NO: 10 or an active fragment of said nucleotide sequence, and a synthetic polynucleotide molecule, capable of suppressing intron 22 cryptic exon inclusion in the mature CFTR mRNA. Each possibility represents a separate embodiment of the present invention.

In specific such embodiments, said kit comprises a synthetic polynucleotide molecule comprising the nucleotide sequence set forth in SEQ ID NO: 10 or an active fragment of said nucleotide sequence, and a synthetic polynucleotide molecule comprising the nucleotide sequence set forth in SEQ ID NO: 6, SEQ ID NO: 7, SEQ ID NO: 8, or SEQ ID NO: 9. Each possibility represents a separate embodiment of the present invention.

In certain embodiments, said synthetic polynucleotide and said additional anti-Cystic-Fibrosis agent are comprised in one or more pharmaceutical compositions. In certain embodiments, said synthetic polynucleotide and said additional anti-Cystic-Fibrosis agent are comprised in the same or different pharmaceutical compositions. In other certain embodiments, said one or more pharmaceutical compositions are each independently formulated for oral, nasal, aerosol, inhalation, abdominal, subcutaneous, intra-peritoneal or intravenous administration. Each possibility represents a separate embodiment of the present invention.

Figure 6:
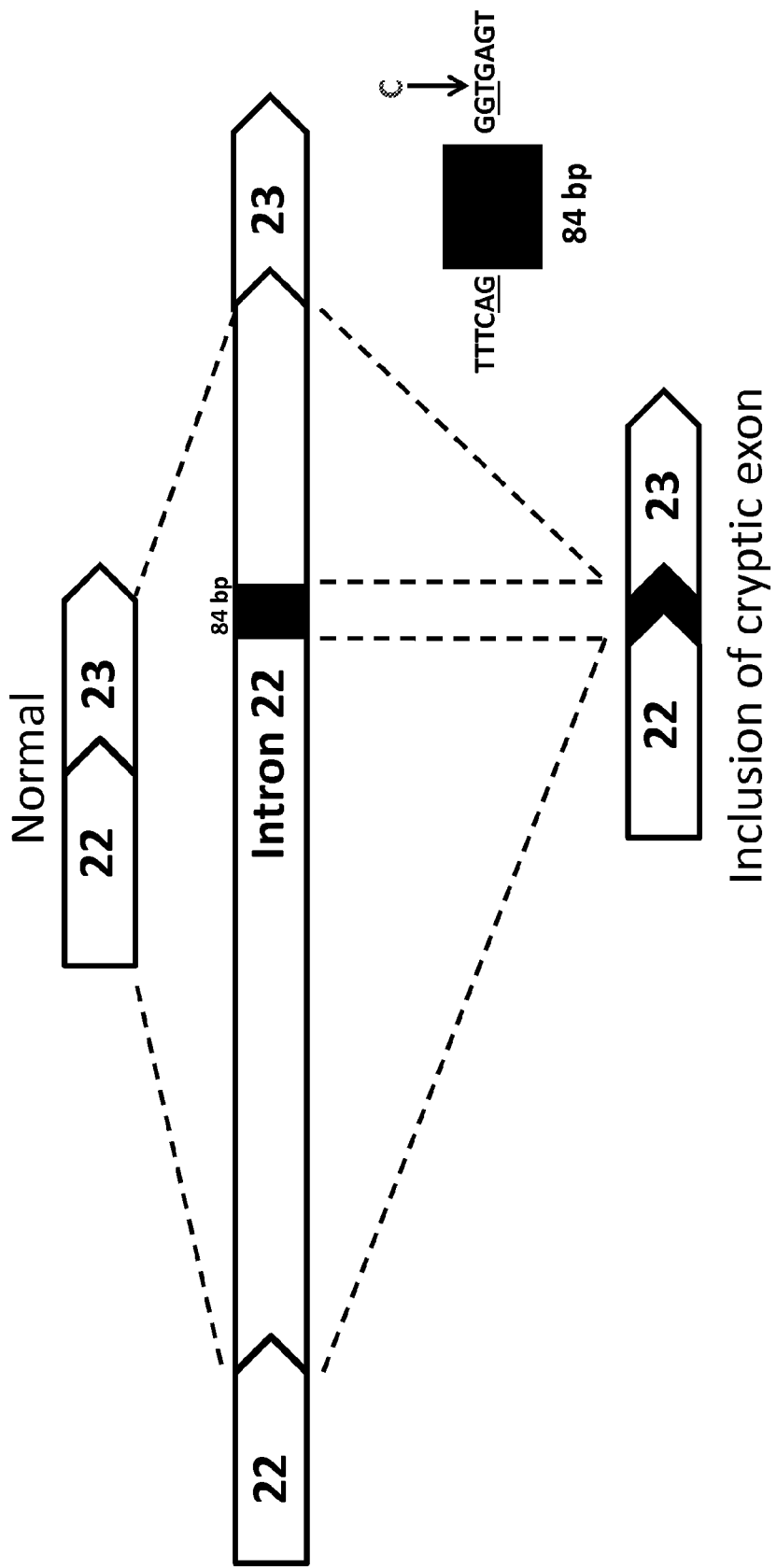
FIG. 6: illustrates the effect of the 3849+10kb C to T mutation in intron 22 of the CFTR gene. Top—upon normal splicing, exon 22 and exon 23 become adjacent. Bottom—a splicing mutation in intron 22 (denoted "3849+10kb C-to-T" mutation) leads to inclusion of an excess of 84 bases in the mature CFTR mRNA (denoted "intron 22 cryptic exon"). The mutation creates a premature in-frame stop codon, leading to mRNA degradation by the nonsense mediated mRNA decay (NMD) mechanism.

In a further aspect, the present invention provides a synthetic polynucleotide molecule, comprising a nucleotide sequence comprising a sequence of at least 20 consecutive nucleotide bases, wherein said synthetic polynucleotide molecule is capable of binding to a pre-mRNA transcript of the CFTR gene, and suppressing intron 22 cryptic exon inclusion in the mature CFTR mRNA. The phrase "suppress intron 22 cryptic exon inclusion" as used herein refers to lowering the occurrence of the addition of 84 nucleotides (SEQ ID NO: 5) found within intron 22 of the CFTR gene to the mature CFTR mRNA, leading to degradation of said mRNA by the nonsense mediated mRNA decay (NMD) mechanism, as illustrated in FIG. 6. In certain embodiments, the nucleotide sequence comprises at least 20 nucleotides e.g. at least 21 nucleotides. In other certain embodiments, the nucleotide sequence comprises about 20 to 30 nucleotides e.g. about 20 to 28, about 20 to 26 or about 22 to 26 nucleotides. In specific embodiments, the nucleotide sequence comprises 22, 23, 24, 25, or 26 nucleotides. Each possibility represents a separate embodiment of the present invention. In certain embodiments, said nucleotide sequence is complementary to the nucleotide sequence set forth in SEQ ID NO: 3, or to a fragment thereof. In certain embodiments, said nucleotide sequence is complementary to the nucleotide sequence set forth in SEQ ID NO: 4, or to a fragment thereof. Each possibility represents a separate embodiment of the present invention. In other certain embodiments, said nucleotide sequence comprises a nucleotide sequence set forth in SEQ ID NO: 6, SEQ ID NO: 7, SEQ ID NO: 8 or SEQ ID NO: 9. Each possibility represents a separate embodiment of the present invention. Specific embodiments of said synthetic polynucleotide molecule are described above.

The present invention further provides, in a related aspect, a pharmaceutical composition comprising a synthetic polynucleotide molecule as described above, and a pharmaceutically acceptable carrier. Specific embodiments of said pharmaceutical composition are described above.

In a further related aspect, the present invention provides a synthetic polynucleotide molecule as described above, for use in the modulation of splicing of a CFTR pre-mRNA. In certain embodiments, said synthetic polynucleotide molecule is for use in reducing the level of an mRNA molecule comprising the nucleotide sequence set forth in SEQ ID NO: 11. In other certain embodiments, said synthetic polynucleotide molecule is for use in increasing the level of an mRNA molecule comprising the nucleotide sequence set forth in SEQ ID NO: 1. In other certain embodiments, said synthetic polynucleotide molecule comprises the nucleotide sequence set forth in SEQ ID NO: 6, SEQ ID NO: 7, SEQ ID NO: 8 or SEQ ID NO: 9. Each possibility represents a separate embodiment of the present invention. Specific embodiments of said use are described above.

The invention further provides, in an aspect, a method for improving at least one clinical parameter of Cystic Fibrosis in a patient in need thereof, comprising the step of administering a therapeutically effective amount of a synthetic polynucleotide molecule as described above to said patient. In certain embodiments, said clinical parameter is selected from the group consisting of lung function, time to the first pulmonary exacerbation, change in weight, change in height, a change in Body Mass Index (BMI), change in the concentration of sweat chloride, number and/or duration of pulmonary exacerbations, total number of days of hospitalization for pulmonary exacerbations, and the need for antibiotic therapy for sinopulmonary signs or symptoms. Each possibility represents a separate embodiment of the present invention. Specific embodiments of said method are described above.

The terms "comprises", "comprising", "includes", "including", "having" and their conjugates mean "including but not limited to". This term encompasses the terms "consisting of" and "consisting essentially of". As used herein, the singular form "a", "an", "the" and "said" include plural references unless the context clearly dictates otherwise. For example, the term "a compound" or "at least one compound" may include a plurality of compounds, including mixtures thereof.

The following examples are meant to be construed as non-limiting to the scope of the invention and are to serve merely as illustrative embodiments.

EXAMPLES

TABLE 1

Sequences.

| SEQ ID NO: | Title | Chr. 7 position | Orientation |
|---|---|---|---|
| 1 | Mature CFTR mRNA | NM_000492.3 (NCBI) | Sense |
| 2 | Exon 10 target | 117188295-117189277 | Sense |
| 3 | Intron 22 target #1 | 117279911-117280032 | Sense |
| 4 | Intron 22 target #2 | 117279906-117280037 | Sense |
| 5 | Intron 22 cryptic exon | 117279930-117280013 | Sense |
| 6 | Oligonucleotide #1 | 117279925-117279949 | Anti-sense |
| 7 | Oligonucleotide #2 | 117279939-117279963 | Anti-sense |
| 8 | Oligonucleotide #3 | 117279975-117279999 | Anti-sense |

TABLE 1-continued

Sequences.

| SEQ ID NO: | Title | Chr. 7 position | Orientation |
|---|---|---|---|
| 9 | Oligonucle-otide #4 | 117280007-117280031 | Anti-sense |
| 10 | Oligonucle-otide #5 | 117188920-117188941 | Anti-sense |
| 11 | Exons 1-27 + cryptic exon 22 | | Sense |
| 12 | Exons 1-9 + 11-27 | | Sense |
| 13 | Control Oligonucleotide #1 | | Anti-sense |

TABLE 1-continued

Sequences.

| SEQ ID NO: | Title | Chr. 7 position | Orientation |
|---|---|---|---|
| 14 | Control Oligonucleotide #2 | | Anti-sense |

TABLE 2

Oligonucleotides.

| Oligonucleotide # | SEQ ID NO: | Nucleotide sequence | Length (nt) |
|---|---|---|---|
| 1 | 6 | aaaucaagaugacaagucaacugaa | 25 |
| 2 | 7 | cuuguggucuccagaaaucaagaug | 25 |
| 3 | 8 | aacagauggaagacucuuguaauua | 25 |
| 4 | 9 | ucagggugucuuacucaccauuuua | 25 |
| 5 | 10 | cuagaaaaaaaagagacaugg | 22 |
| 6 | 13 | cuugugaaacuuacugauuaucagg | 25 |
| 7 | 14 | ccucuuaccucaguuacaauuuaua | 25 |

Methods

Oliconucleotide Synthesis

2-O-Methyl modified oligonucleotides on a phosphorothioate backbone were synthesised on an Expedite 8909 Nucleic Acid Synthesiser (Life Technologies) using the 1umol thioate synthesis protocol according to the pre-programmed synthesis manual. The synthesis protocols are pre-loaded on the Synthesizer.

Cell Culture and Transfection Protocol for Intron 22 Cryptic Exon Exclusion

CFP15a nasal epithelial cell line, established from a patient heterozygous for W1282X and 3849+10 kb C to T mutations, were grown in Bronchial Epithelial Cell Basal medium (Lonza). One day prior to transfection, the cells were plated onto 140 mm plates with 400,000 cells per plate. On the day of transfection, the medium was replaced to opti-MEM (Invitrogen) with no additional supplements. Cells were transfected with 2-O-methyl AO lipoplexes (Lipofcetamin:AO ratio of 1:1) with AO concentrations of 25 nM or 10 nM and left to incubate at 37° C. for 24 hours. After 4 hours of incubation, the transfection medium was replaced with fresh Bronchial Epithelial Cell Basal medium.

RNA Analysis

TABLE 3

Primer Sequences

| Primer | Primer location | Sequence 5'→3' (SEQ ID NO) |
|---|---|---|
| 1[a] | External CFTR Fwd | AGCATTTGCTGATTGCACAG (15) |
| 2[a] | External CFTR Rev | GAAAGAGCTTCACCCTGTCG (16) |
| 3[b] | Short CFTR (ex 26) Fwd | AATGCTGGAATGCCAACAATT (17) |
| 4[b] | Short CFTR (ex 27) Rev | GGCTCCTCTCGTTCAGCAGT (18) |
| 5[a] | 84 external Fwd (exon 22) | GGGCCAAATGACTGICAAAG (19) |
| 6[a] | 84 external Rev (84bp) | GCAACAGATGGAAGACTCTTGT (20) |
| 7[b] | TPW Fwd (exon 22) | GCCATATTAGAGAACATTTCCTTCTCA (21) |
| 8[b] | TPW Rev (84 bp) | ACCTTGTGGTCTCCAGAAATCAA (22) |

[a]-RT-PCR;
[b]-nested PCR.

Total RNA was extracted using the RNeasy extraction kit (QIAGEN). RNA-less and reverse-transcriptase-less reactions were used as controls. 1000 ng of total RNA was used for complementary DNA (cDNA) synthesis using the High Capacity cDNA Reverse Transcription Kit (Applied Biosystems). 1 µl of cDNA was used for RT-PCR (Invitrogen Amplitaq enzyme kit) using outer primers targeting sequences at the extremities of exons 26/27 (primers 1 and 2) and of exon 22/84 bp pseudo exon (primers 5 and 6). Samples were incubated at 94° C. for 1:45 min, followed by 35 cycles (for 84 bp variant amplification) or 30 cycles (for total CFTR amplification) of 94° C. for 30 sec, 55° C. for 30 sec and 72° C. for 1 min. Samples were diluted 1/27 and 1/81 and 3 µl were used for nested PCR for second amplification using primers targeting internal regions across exon 22/84 bp pseudo exon (for 84 bp variant amplification, primers 7 and 8) or exons 26/27 (for total CFTR amplification, primers 3 and 4). RT-PCR was performed in ABI 7500 using a Power SYBR green PCR master Mix (Applied Biosystems). The expression level was normalized to the transcript levels of POLR2A and IPO8. Specific printers for these PCR reactions were designed using the Primer Express software. For statistical analysis Student t-test was used.

Transfection Protocol for Exon 10 Inclusion

16HBE normal bronchiole epithelial cell line shows low levels of exon 10 skipping. Cells were propagated in 10% FCS DMEM, supplemented with L-Glutamine and penicillin/streptomycin/fungizome. 16HBE cells plated onto 24 well plates with 50,000 cells per well with 10% FCS DMEM with 2 wells per treatment, and left overnight prior to transfection.

16HBE cells were transfected with 2-O-methyl oligonucleotide lipoplexes (Lipofectin:AO ratio of 2:1) with oligonucleotide concentrations of 600 nM, 300 nM and 150 nM, topped up to 1 ml with 1% FCS DMEM (no additional supplements) and left to incubate at 37° C. for 48 hours.
Nested PCR and RT-PCR Protocols

TABLE 4

Primer Sequences

| Primer | Primer location | Sequence (SEQ ID NO) |
|---|---|---|
| 9[a] | MR exon 8 Fwd | GGT TCT TTG TGG TGT TTT TAT CT (23) |
| 10[a] | CFTR exon 8/9 Fwd | GCA ATA AAC AAA ATA CAG GAT TTC (24) |
| 11[a] | CFTR exon 11/12 Rev | AAA CTT GGA GAT GTC CTC TTC (25) |
| 12[b] | CPTR exon 12 Rev | TGC TAA AGA AAT TCT TGC TCG TT (26) |

[a]-nested PCR:
[b]-RT-PCR.

Following transfection, cells were harvested and RNA extracted using TriZol reagent as per manufacturer's instruction. 200 ng of total RNA was used for nested PCR. Primary PCR setup using Invitrogen One Step RT-PCR SuperScript III with Platinum Taq enzyme kit as per manufacturer's instruction, amplified with primers targeting exons 8-12 (primers 9 and 12). Samples were incubated at 55° C. for 30 min, 94° C. for 2 min, followed by 35 cycles of 94° C. for 40 sec, 58° C. for 1 min and 68° C. for 1 min. Samples were diluted 1/10 and 1 µl used for secondary amplification using Invitrogen AmpliTaQ Gold enzyme kit, as per manufacturer instructions. Samples were amplified across exon 8/9 to 11/12 boundaries (primers 10 and 11) and incubated at 94° C. for 6 min, followed by 30 cycles of 94° C. for 40 sec, 55° C. for 1 min and 72° C. for 1 min. Samples were fractionated on 2% Agarose gels, and products visualized on a Chemismart-3000 gel documentation system. Product identity was confirmed by band purification and DNA sequencing as necessary.

Halide Efflux Assay (SPQ) Protocol

Cells were seeded onto collagen-coated glass coverslips and grown to ~80% confluence. Immediately prior to study, cells were hypotonically loaded with halide quenched dye 6-methoxy-N-(3-sulfopropyl)quinolinium (SPQ), 10 mM, Molecular Probes Inc., Eugene, Oreg.) for 10 min and then placed in a quenching NaI-based buffer (King & Sorscher, Biochemistry, 2000). CFTR robustly conducts iodide in addition to chloride, $HCO_3^-$, and other anions, allowing use of iodide quench as a measure of macroscopic channel activity. Cells were mounted in a specially designed perfusion chamber and fluorescence monitored using an inverted microscope. Baseline fluorescence was initially studied in NaI buffer (above) followed by dequenching $NaNO_3$ solution (King & Sorscher, Biochemistry, 2000). CFTR agonists (20 µM forskolin, 50 µM genistein) were added to activate channel gating, after which NaI buffer was again perfused. Fluorescence was normalized for each cell versus baseline and increases shown as percent above basal (quenched) values. For each coverslip, >15 individual cells were monitored. Averages from each coverslip were used for statistical analysis.

Example 1

Figure 3:
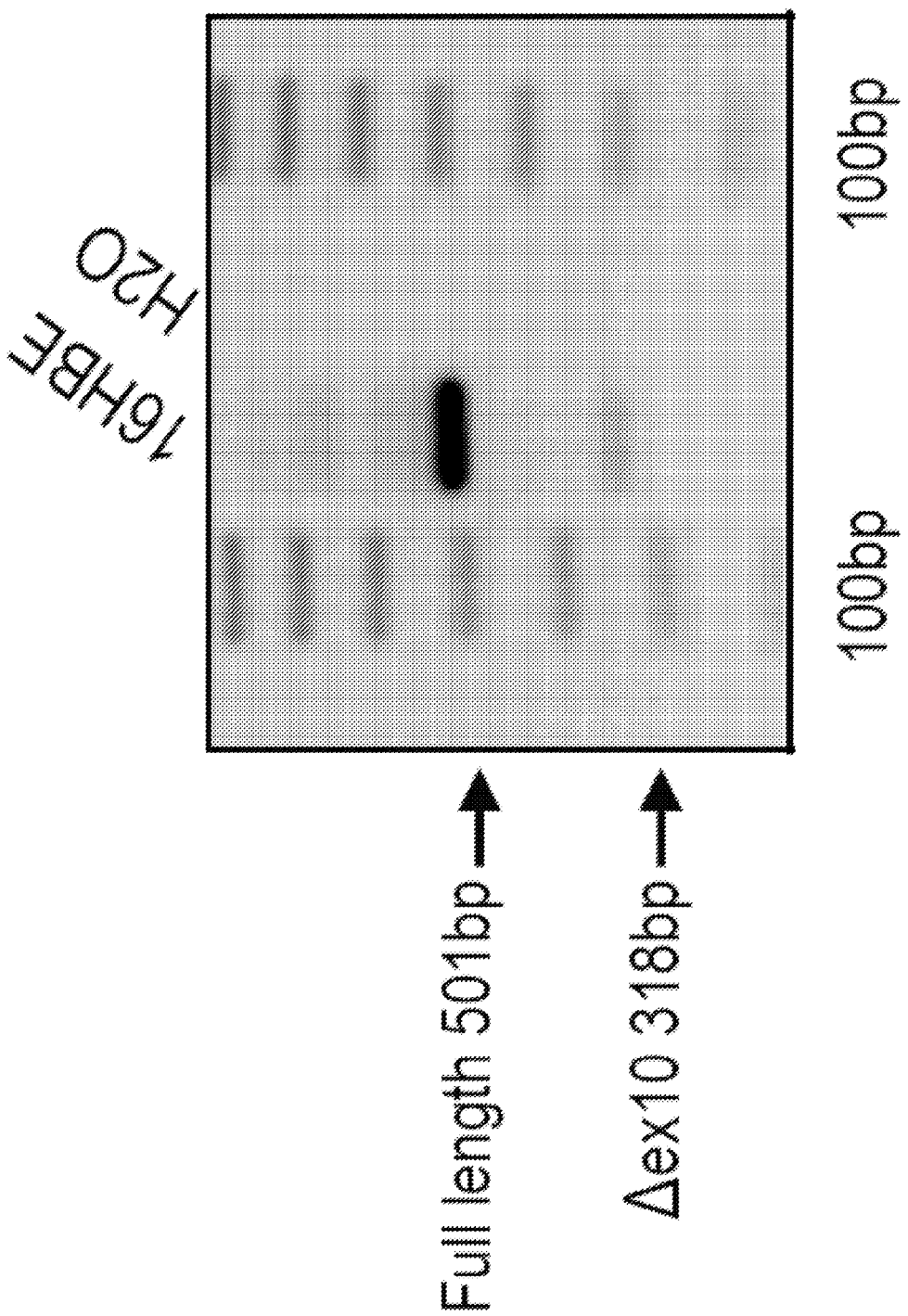
FIG. 3: illustrates the levels of base-line exon 10 skipping in untreated 16HBE cells.
Figure 4:
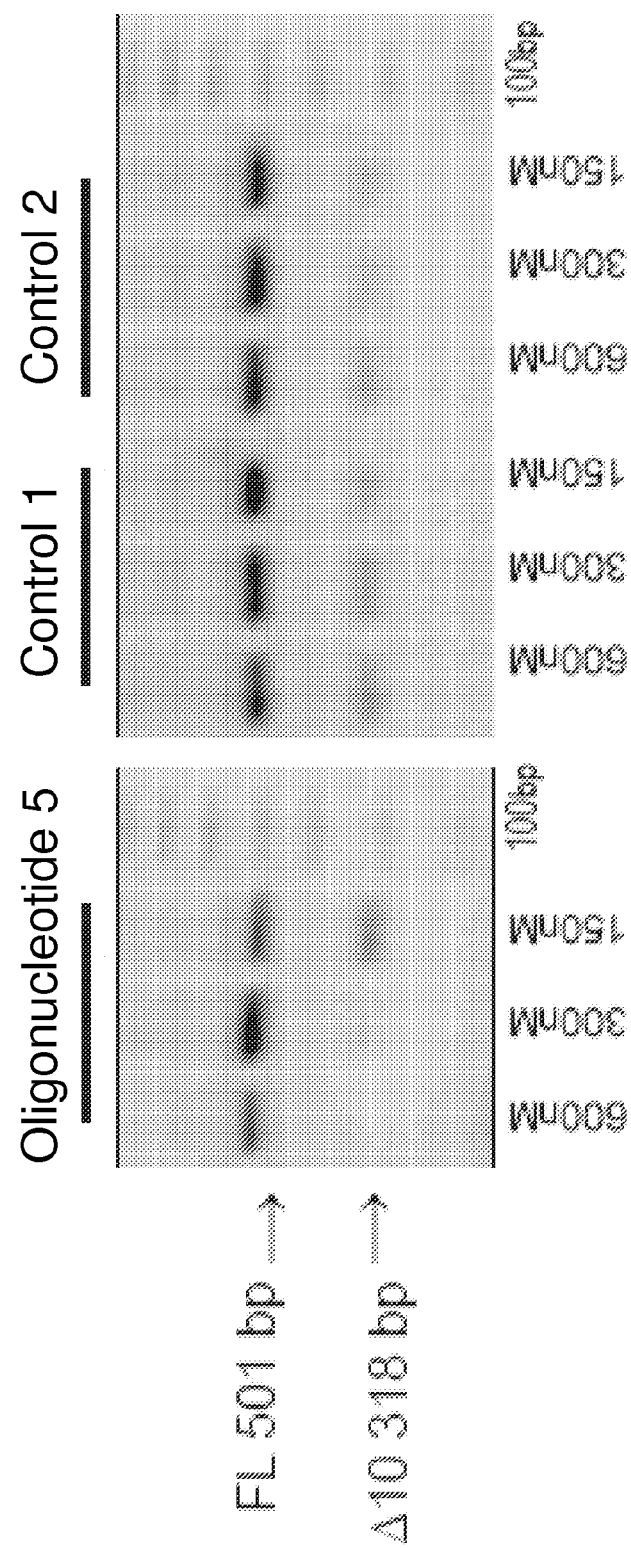
FIG. 4: illustrates the effect of oligonucleotide 5 on the correct splicing of exon 10 of the CFTR gene. FL 501 bp—variant comprising exon 10. Δ 10 318 bp—variant without exon 10.

Oligonucleotide No. 5 was synthesized and tested for its anti-splicing-silencing capability, i.e. its ability to minimize exon 10 skipping and increase exon 10 inclusion in the mature CFTR mRNA in 16HBE cells (see FIG. 3). FIG. 4 depicts that oligonucleotide no. 5 was indeed able to dramatically increase the level of exon 10 inclusion in the mature CFTR mRNA in a dose dependent manner, as clearly evident from the progressive strengthening of the full 501-base transcripts and the progressive weakening and eventually loss of the aberrant Δ exon 10 318-base transcripts.

The data presented in FIG. 4 provides substantial evidence, for the first time, that exon 10 splicing may be modulated by oligonucleotides targeting sequences within and adjacent to exon 10 (as illustrated in FIG. 2).

Example 2

Figure 7:
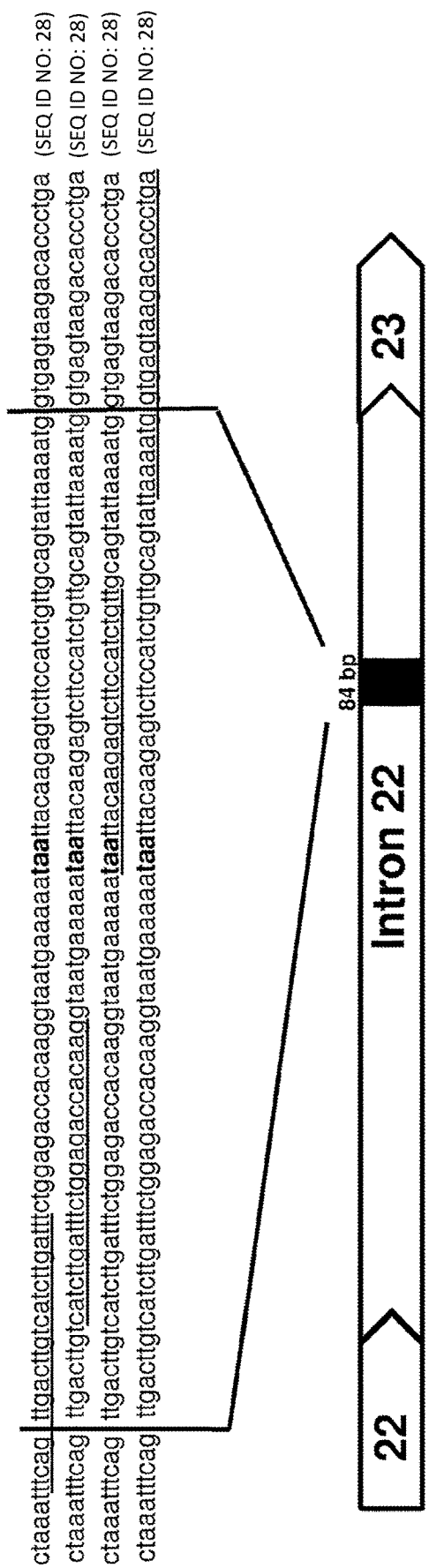
FIG. 7: illustrates the binding sites (underlined) of oligonucleotides 1-4 within the 84 bases cryptic exon (oligonucleotides 2 and 3), or at the junctions between intron 22 and the internal cryptic exon (oligonucleotides 1 and 4) in a CFTR allele carrying the 3849+10kb C to T mutation. Bold—a premature in-frame stop codon.
Figure 8A:
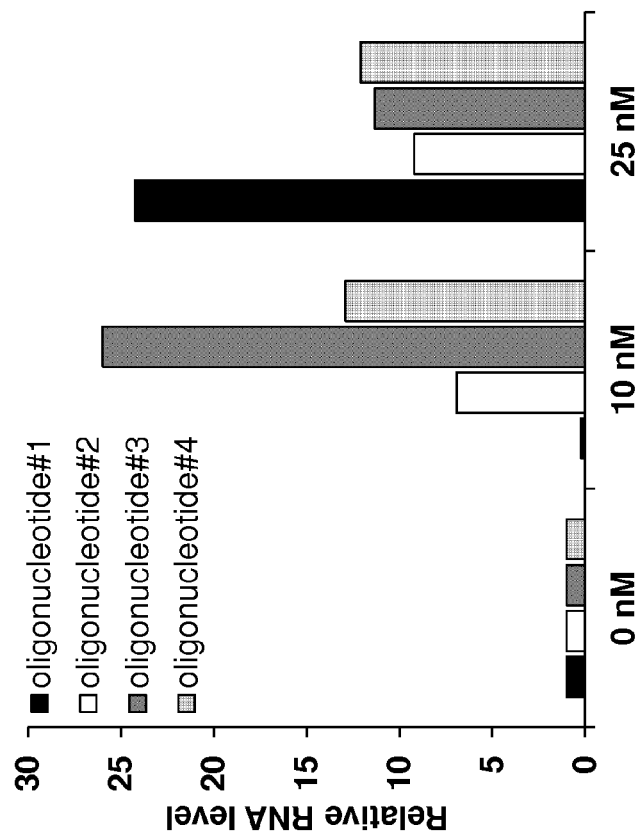
FIG. 8A-8B: illustrates the effect of oligonucleotides 1-4 on (8A) CFTR 84 bp splicing variant mRNA levels, and on (8B) total CFTR mRNA levels. Specific oligonucleotides were transfected (Lipofectamine, Invitrogen) into CFP15a epithelial cell line carrying the 3849+10kb C to T splicing mutation (transfection concentration: 10 nM and 25 nM). Total RNA was extracted from the cells 24 hours after transfection and cDNA was amplified by RT-PCR followed by nested PCR. Following oligonucleotides treatment, a marked elevation in the level of correctly spliced transcript (total CFTR) was observed. Under the same conditions aberrantly spliced transcripts were undetectable.
Figure 8B:
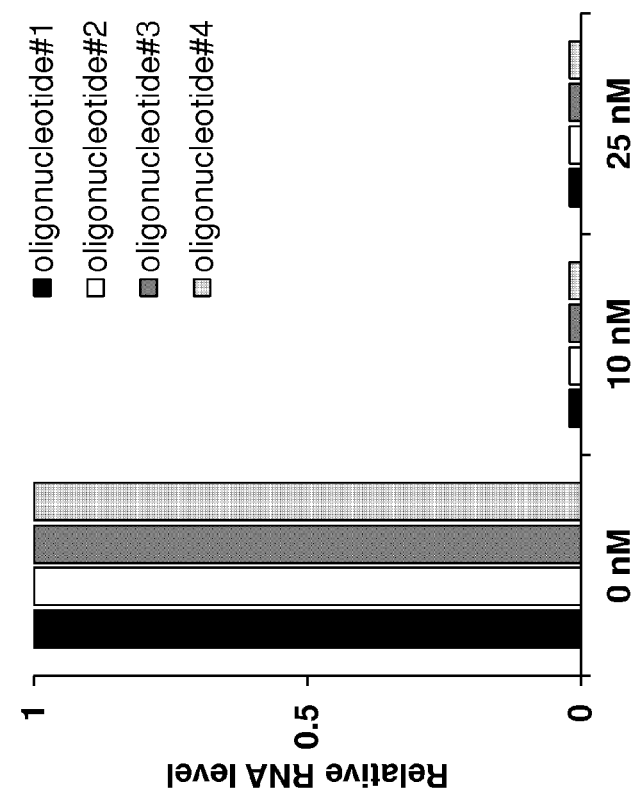

Epithelial cell line CFP15a, established from a nasal polyp of a Cystic Fibrosis patient carrying the 3849+10kb C to T splicing mutation, were transfected with various concentrations of oligonucleotides 1-4 as described above (see FIG. 7). After 4 hours of incubation, the transfected medium was replaced with fresh medium. Twenty four hours after transfection, the cells were harvested for RNA extraction, followed by cDNA synthesis. Aliquots of cDNA were used for RT-PCR using two pairs of outer primers towards exon 22 and the 84 bp cryptic exon (primers 5-6 in Table 3) and towards exon 26-27 (for total CFTR evaluation, primers 1-2 in Table 3). Nested PCR was subsequently performed using internal primers (primers 7-8 for the detection of the 84 bp cryptic exon, and primers 3-4 for the evaluation of total CFTR level). FIG. 8A depicts that oligonucleotides 1-4 completely prevented the formation of the CFTR 84 bp splicing variant in the transfected cells in both concentrations (25 and 10 nM). FIG. 8B depicts that oligonucleotides 1-4 were further able to dramatically increase by several folds the level of total CFTR mRNA.

From the data presented in FIG. 8A-B it becomes evident that oligonucleotides according to the present invention are capable of binding to their predetermined targets and significantly modify the CFTR splicing balance in cells carrying the 3849+10kb C to T splicing mutation in favor of the full CFTR transcript.

Example 3

Figure 9:
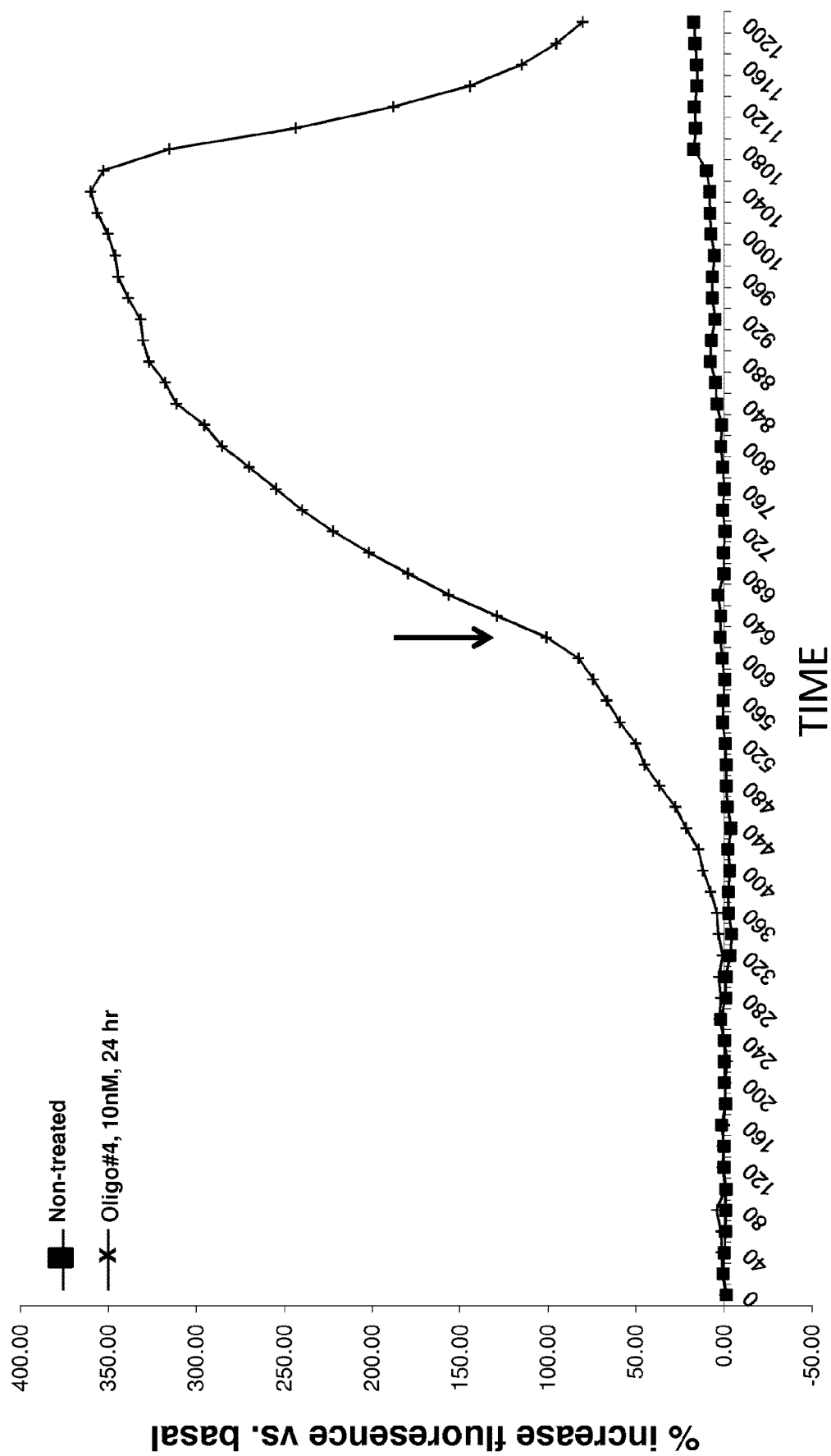
FIG. 9: illustrates the effect of oligonucleotide 4 on the restoration of the CFTR protein function. CFP15a epithelial cell line, carrying the 3849+10kb C to T splicing mutation, were transfected with oligonucleotide 4 for 24 hours (transfection concentration: 10 nM). Following transfection, the cells were analyzed for functional CFTR activity using the halide efflux assay (SPQ). Following the oligonucleotide treatment, a significant restoration of the CFTR activity was observed. Arrow—the addition of Forskolin and Genestein, two CFTR channel activators. The extent of fluorescence is correlated with CFTR channel activation. Fluorescence was normalized versus baseline. The CFTR functional analysis of a representative cell is shown.

In addition to the experimental results provided in Example 2, CFP15a epithelial cells were transfected with oligonucleotide 4 for 24 hours (transfection concentration: 10 nM). Following transfection, the cells were analyzed for functional CFTR activity using the halide efflux assay (SPQ). Following treatment, a significant restoration of the CFTR protein activity was observed. The extent of fluorescence is correlated with CFTR channel activation. FIG. 9 depicts that as soon as 24 hours post oligonucleotide transfection, functional CFTR chloride channels responsible for chloride transport were embedded in the epithelial cells' membrane resulting in restored CFTR function.

To further verify this result, forskolin and genestein (CFTR channel activators) were added, since their addition, pending that the CFTR channel is present on the cell membrane and is functional, will cause the channel to open and allow chloride efflux. FIG. 9 depicts that the fluorescent signal has increased following the addition of the activators, attributed to chloride efflux through the CFTR channel.

It is therefore evident that the administration of oligonuclotides according to the present invention is capable of substantially increasing the CFTR function in cells carrying the 3849+10kb C to T splicing mutation.

REFERENCES

Cirak, S., Arechavala-Gomeza, V., Guglieri, M., Feng, L., Torelli, S., Anthony, K., Abbs, S., et al. (2011). Exon skipping and dystrophin restoration in patients with Duchenne muscular dystrophy after systemic phosphorodiamidate morpholino oligomer treatment: an open-label, phase 2, dose-escalation study. Lancet, 378(9791), 595-605. doi:10.1016/S0140-6736(11)60756-3

Chu C. H., Trapnell B. C., Curristin S., Cutting G. R. and Crystal R. G. (2003). Genetic basis of variable exon 9 skipping in cystic fibrosis transmembrane conductance regulator mRNA. Nature genetics, Vol. 3, 151-156

Cutting, G. R. (1990). A cluster of cystic fibrosis mutations in the first nucleotide-binding fold of the cystic fibrosis conductance regulator protein. Nature, 346(6282), 366-369

Friedman, K. J., Kole, J., Cohn, J. A., Knowlesi, M. R., Silverman, L. M. and Ryszard Kole (1999). Correction of Aberrant Splicing of the Cystic Fibrosis Transmembrane Conductance Regulator (CFTR) Gene by Anti-sense Oligonucleotides. THE JOURNAL OF BIOLOGICAL CHEMISTRY, Vol. 274(51), 36193-36199

Gebski, B. L., Mann, C. J., Fletcher, S., & Wilton, S. D. (2003). Morpholino anti-sense oligonucleotide induced dystrophin exon 23 skipping in mdx mouse muscle. Human molecular genetics, 12(15), 1801-11.

Goemans, N. M., Tulinius, M., van den Akker, J. T., Burm, B. E., Ekhart, P. F., Heuvelmans, N., Holling, T., et al. (2011). Systemic administration of PRO051 in Duchenne's muscular dystrophy. The New England journal of medicine, 364(16), 1513-22. doi:10.1056/NEJMoa1011367

Goyenvalle, A., Babbs, A., Powell, D., Kole, R., Fletcher, S., Wilton, S. D., & Davies, K. E. (2010). Prevention of dystrophic pathology in severely affected dystrophin/utrophin-deficient mice by morpholino-oligomer-mediated exonskipping. Molecular therapy: the journal of the American Society of Gene Therapy, 18(1), 198-205. doi:10.1038/mt.2009.248

Groman J. D. et al., (2004). Variation in a Repeat Sequence Determines Whether a Common Variant of the Cystic Fibrosis Transmembrane Conductance Regulator Gene Is Pathogenic or Benign. Am. J. Hum. Genet., Vol. 74:176-179

Hefferon T. W., Groman J. D., Yurk C. E., and Cutting G. R. (2004). A variable dinucleotide repeat in the CFTR gene contributes to phenotype diversity by forming RNA secondary structures that alter splicing. PNAS, Vol. 101(10), 3504-3509

Hua, Y., Sahashi, K., Hung, G., Rigo, F., Passini, M. A., Bennett, C. F., & Krainer, A. R. (2010). Anti-sense correction of SMN2 splicing in the CNS rescues necrosis in a type III SMA mouse model. Genes & development, 24(15), 1634-44. doi:10.1101/gad.1941310

Kerem E., Nissim-Rafinia M., Argaman Z., Augarten A., Bentur L., Klar A., Yahav Y., Szeinberg A., Hiba O., Branski D., Corey M., and Kerem B. (1997). A Missense Cystic Fibrosis Transmembrane Conductance Regulator Mutation With Variable Phenotype. Pediatrics, Vol. 100 (3), 1-6

Kerem, B. S (1990). Identification of mutations in regions corresponding to the two putative nucleotide (ATP)-binding folds of the cystic fibrosis gene. Proceedings of the National Academy of Sciences of the United States of America, Vol. 87(21), 8447-8451

Kiesewetter S., Macek M., Davis C., Curristin S. M., Chu C. S., Graham C., Shrimpton A. E., Cashman S. M., Tsui L. C., Mickle J., Amos J., Highsmith W. E., Shuber A., Witt D. R., Crystal R. G. and Cutting G. R. (1993). A mutation in CFTR produces different phenotypes depending on chromosomal background. Nature Genetics, Vol. 5, 274-278. doi:10.1038/ng1193-274

Kinali, M., Arechavala-Gomcza, V., Feng, L., Cirak, S., Hunt, D., Adkin, C., Guglieri, M., et al. (2009). Local restoration of dystrophin expression with the morpholino oligomer AVI-4658 in Duchenne muscular dystrophy: a single-blind, placebocontrolled, dose-escalation, proof-of-concept study. Lancet neurology, 8(10), 918-28. doi: 10.1016/S1474-4422(09)70211-X Lorson, C. L., Rindt, H., & Shababi, M. (2010). Spinal muscular atrophy: mechanisms and therapeutic strategies. Human molecular genetics, 19(R1), R11-8. doi:10.1093/hmg/ddq147

Lu Q. L., Yokota T., Takeda S., Garcia L., Muntoni F. and Partridge T. (2011). The Status of Exon Skipping as a Therapeutic Approach to Duchenne Muscular Dystrophy. Molecular Therapy, Vol. 19(1). 9-15

Mann, C. J., Honeyman, K., Cheng, A. J., Ly, T., Lloyd, F., Fletcher, S., Morgan, J. E., et al. (2001). Anti-sense-induced exon skipping and synthesis of dystrophin in the mdx mouse. Proceedings of the National Academy of Sciences of the United States of America, 98(1), 42-7. doi:10.1073/pnas.011408598

Mendell J. R., Rodino-Klapac L. R., Sahenk Z., Roush K., Bird L., Lowes L. P., Alfano L., Gomez A. M., Lewis S., Kota J., Malik V., Shontz K., Walker C. M., Flanigan K. M., Corridore M., Kean J. R., Allen H. D., Shilling C., Melia K. R., Sazani P., Saoud J. B., Kaye E. M.; the Eteplirsen Study Group (2013). Eteplirsen for the treatment of Duchenne muscular dystrophy. Ann Neurol. 2013 Aug. 1.

Mitrpant, C., Adams, A. M., Meloni, P. L., Muntoni, F., Fletcher, S., & Wilton, S. D. (2009). Rational design of anti-sense oligomers to induce dystrophin exon skipping. Molecular therapy: the journal of the American Society of Gene Therapy, 17(8), 1418-26. doi:10.1038/mt.2009.49

Porensky, P. N., Mitrpant, C., McGovern, V. L., Bevan, A. K., Foust, K. D., Kaspar, B. K., Wilton, S. D., et al. (2012). A single administration of morpholino anti-sense oligomer rescues spinal muscular atrophy in mouse. Human molecular genetics, 21(7), 1625-38. doi:10.1093/hmg/ddr600

Rogan M. P., Stoltz D. A. and Hornick D. B. (2011). Cystic Fibrosis Transmembrane Conductance Regulator Intracellular Processing, Trafficking, and Opportunities for Mutation-Specific Treatment. CHEST, Vol. 139(6), 1480-1490. doi:10.1378/chest.10-2077

Singh, N. N., Shishimorova, M., Cao, L. C., Gangwani, L., & Singh, R. N. (2009). A short anti-sense oligonucleotide masking a unique intronic motif prevents skipping of a critical exon in spinal muscular atrophy. RNA biology, 6(3), 341-50.

Williams, J. H., Schray, R. C., Patterson, C. A., Ayitey, S. O., Tallent, M. K., & Lutz, G. J. (2009). Oligonucleotide-mediated survival of motor neuron protein expression in CNS improves phenotype in a mouse model of spinal muscular atrophy. The Journal of neuroscience: the official journal of the Society for Neuroscience, 29(24), 7633-8. doi:10.1523/JNEUROSCI.0950-09.2009 van Deutekom, J. C., Janson, A. A., Ginjaar, I. B., Frankhuizen, W. S., Aartsma-Rus, A., Bremmer-Bout, M., den Dunnen, J. T., et al. (2007). Local dystrophin restoration with anti-sense oligonucleotide PRO051. The New England journal of medicine, 357(26), 2677-86. doi:10.1056/NEJMoa073108

The invention claimed is:

1. A pharmaceutical composition formulated for administration to a subject, comprising a chemically modified synthetic polynucleotide molecule which comprises a nucleotide sequence having a sequence of at least 18 consecutive nucleotide bases, wherein said synthetic polynucleotide molecule is specific for and binds to a pre-messenger RNA (pre-mRNA) transcript of the Cystic Fibrosis Transmembrane conductance Regulator (CFTR) gene and suppresses exon 10 exclusion from the mature CFTR mRNA, and wherein said nucleotide sequence is complementary to the nucleotide sequence set forth in SEQ ID NO: 2, or to a fragment thereof.

2. The synthetic polynucleotide molecule of claim 1, wherein said nucleotide sequence is complementary and specific to an exon 10 of CFTR splicing silencing motif.

3. The pharmaceutical composition of claim 1, wherein said nucleotide sequence comprises a nucleotide sequence set forth in SEQ ID NO: 10 or an active fragment of said nucleotide sequence.

4. The pharmaceutical composition of claim 1, further comprising a pharmaceutically acceptable carrier.

5. The pharmaceutical composition of claim 1, wherein said administration is oral, nasal, aerosol, inhalation, abdominal, subcutaneous, intra-peritoneal or intravenous.

6. A method for improving at least one clinical parameter of Cystic Fibrosis in a patient in need thereof, comprising the step of administering a therapeutically effective amount of the pharmaceutical composition according to claim 1 to said patient.

7. The method of claim 6, wherein said synthetic polynucleotide molecule comprises the nucleotide sequence set forth in SEQ ID NO: 10, or an active fragment of said nucleotide sequence.

8. A kit comprising:
(i) the pharmaceutical composition according to claim 1, and
(ii) an additional anti-Cystic-Fibrosis agent.

9. A chemically modified synthetic polynucleotide molecule, comprising the nucleotide sequence set forth in SEQ ID NO: 6, SEQ ID NO: 7, SEQ ID NO: 8, or SEQ ID NO: 9, or an active fragment thereof, wherein said synthetic polynucleotide molecule binds to a pre-mRNA transcript of the Cystic Fibrosis Trans-membrane conductance Regulator (CFTR) gene, and suppresses intron 22 cryptic exon inclusion in the mature CFTR mRNA.

10. A pharmaceutical composition comprising the synthetic polynucleotide molecule according to claim 9, and a pharmaceutically acceptable carrier.

11. A method for improving at least one clinical parameter of Cystic Fibrosis in a patient in need thereof, comprising the step of administering a therapeutically effective amount of the synthetic polynucleotide molecule according to claim 9 to said patient.

12. A kit comprising:
(i) the chemically modified synthetic polynucleotide molecule according to claim 9, and
(ii) an additional anti-Cystic-Fibrosis agent.

13. The pharmaceutical composition of claim 1, wherein said chemical modification comprises a chemically modified backbone selected from: a phosphorothioate backbone, a 2'-O-methyl-phosphorothioate (2OMP) backbone, a phosphorodiamidate morpholino (PMO) backbone, a peptide nucleic acid (PNA) backbone, a 2-methoxyethyl phosphorothioate (MOE) backbone, and an alternating locked nucleic acids (LNAs) backbone.

14. The synthetic polynucleotide molecule of claim 9, wherein said chemical modification comprises a chemically modified backbone selected from: a phosphorothioate backbone, a 2'-O-methyl-phosphorothioate (2OMP) backbone, a phosphorodiamidate morpholino (PMO) backbone, a peptide nucleic acid (PNA) backbone, a 2-methoxyethyl phosphorothioate (MOE) backbone, and an alternating locked nucleic acids (LNAs) backbone.

15. The pharmaceutical composition of claim 1, consisting of 18 to 30 nucleotides.

16. The pharmaceutical composition of claim 1, wherein the synthetic polynucleotide molecule only affects the CFTR sequence in a cell of said subject.

17. The pharmaceutical composition of claim 1, wherein said chemical modification improves a pharmacokinetic property of said synthetic polynucleotide molecule.

18. The pharmaceutical composition of claim 1, wherein said chemical modification improves biological stability of said synthetic polynucleotide molecule.

19. The pharmaceutical composition of claim 18, wherein said biological stability is within a cell.

20. The pharmaceutical composition of claim 1, wherein said nucleotide sequence is complementary to the nucleotide sequence set forth in SEQ ID NO: 27, or to a fragment thereof.

* * * * *